(12) United States Patent
Kim et al.

(10) Patent No.: US 7,094,569 B2
(45) Date of Patent: Aug. 22, 2006

(54) HAIR FOLLICLE GROWTH FACTOR PROTEINS

(76) Inventors: Soogyun Kim, Unchon Bldg. 4th Fl., 125-14, Chungdam-dong, Gangnam-gu, Seoul (KR) 135-100; Hyun-Jun Jang, Taeyang Villa 201, 30/7 Shingil-dong 253-259, Youngdeungpo-gu, Seoul (KR) 15-050

( * ) Notice: Subject to any disclaimer, the term of this patent is extended or adjusted under 35 U.S.C. 154(b) by 559 days.

(21) Appl. No.: 10/155,292

(22) Filed: May 24, 2002

(65) Prior Publication Data

US 2003/0036174 A1    Feb. 20, 2003

(30) Foreign Application Priority Data

May 24, 2001    (KR) .................... 10-2001-0028621

(51) Int. Cl.
| | |
|---|---|
| A61K 38/18 | (2006.01) |
| C07K 14/50 | (2006.01) |
| C12N 15/12 | (2006.01) |
| C12N 15/63 | (2006.01) |
| C12N 1/21 | (2006.01) |

(52) U.S. Cl. .................... 435/69.1; 435/71.1; 435/325; 435/243; 435/252.8; 435/320.1; 514/12; 530/350; 530/399

(58) Field of Classification Search ............... 435/69.1, 435/320.1, 243, 325; 530/350, 399; 514/2, 514/12; 536/23.5
See application file for complete search history.

(56) References Cited

U.S. PATENT DOCUMENTS

| | | | |
|---|---|---|---|
| 4,599,311 A | 7/1986 | Kawasaki | 435/71 |
| 4,868,116 A | 9/1989 | Morgan et al. | 435/240.2 |
| 4,980,286 A | 12/1990 | Morgan et al. | 435/172.3 |
| 5,149,655 A | 9/1992 | McCabe et al. | 435/287 |
| 5,184,605 A | 2/1993 | Grzeszykowski | 128/24 |
| 5,206,152 A | 4/1993 | Sukhatme | 435/69.1 |
| 5,422,120 A | 6/1995 | Kim | 424/450 |
| 5,547,871 A | 8/1996 | Black et al. | 435/240.1 |
| 5,580,859 A | 12/1996 | Felgner et al. | 514/44 |
| 5,824,643 A | 10/1998 | Pierce et al. | 514/12 |
| 5,965,530 A | 10/1999 | Pierce et al. | 514/12 |
| 6,015,686 A | 1/2000 | Dubensky, Jr. et al. | 435/69.1 |
| 6,077,692 A | 6/2000 | Ruben et al. | 435/69.4 |
| 6,140,111 A | 10/2000 | Rivière et al. | 435/320.1 |
| 6,187,305 B1 | 2/2001 | Treco et al. | 424/93.21 |
| 6,225,290 B1 | 5/2001 | German et al. | 514/44 |
| 6,271,436 B1 | 8/2001 | Piedrahita et al. | 800/21 |
| 6,281,408 B1 | 8/2001 | Khillan | 800/21 |
| 6,291,212 B1 | 9/2001 | Sledziewski et al. | 435/69.1 |
| 6,291,740 B1 | 9/2001 | Bremel et al. | 800/23 |
| 6,468,986 B1 | 10/2002 | Zuckermann et al. | 514/44 |

FOREIGN PATENT DOCUMENTS

| | | |
|---|---|---|
| EP | 0 171 142 B1 | 2/1986 |
| EP | 0 230 023 B1 | 7/1987 |
| EP | 0 272 277 B1 | 6/1988 |
| WO | WO 89/02468 | 3/1989 |
| WO | WO 89/05345 | 6/1989 |
| WO | WO 89/07136 | 8/1989 |
| WO | WO 90/06997 | 6/1990 |
| WO | WO 90/08832 | 8/1990 |
| WO | WO 90/11092 | 10/1990 |
| WO | WO 91/14445 | 10/1991 |
| WO | WO 92/11033 | 7/1992 |
| WO | WO 94/17810 | 8/1994 |
| WO | WO 94/23697 | 10/1994 |
| WO | WO 94/23744 | 10/1994 |
| WO | WO 95/13796 | 5/1995 |

OTHER PUBLICATIONS

Ijima K et al., (2001) "Successful Gene Therapy via Intraarticular Injection of Adenovirus Vector Containing CTLA4IgG in a Murine Model of Type II Collagen-Induced Arthritis" *Human Gene Therapy* 12:1063-1077.
Nishimura T et al., (2000) "Identification of a novel FGF, FGF-21, preferentially expressed in the liver" *Biochimica et Biophysica Acta* 1492: 203-206.
Botchkarev VA et al.,(1999) "Noggin is a mesenchymally derived stimulator of hair-follicle induction" *Nature Cell Biology* 1:158-164.
Chiang C et al., (1999) "Essential Role for *Sonic hedgehog* during Hair Follicle Morphogenesis" *Developmental Biology* 205:1-9.
Gat U et al., (1998) "De Novo Hair Follicle Morphogenesis and Hair Tumors in Mice Expressing a Truncated β-Catenin in Skin" *Cell* 95:605-614.
Martin GR (1998) "The roles of FGFs in the early development of vertebrate limbs" *Genes & Development* 12:1571-1586.
Igarashi M et al., (1998) Characterization of Recombinant Human Fibroblast Growth Factor (FGF)-10 Reveals Functional Similarities with Keratinocyte Growth Factor (FGF-7) *The Journal of Biological Chemistry* 273(21):13230-13235.

(Continued)

*Primary Examiner*—Christine J. Saoud
(74) *Attorney, Agent, or Firm*—Arent Fox PLLC

(57) ABSTRACT

The present invention relates to novel hair follicle growth factor (HFGF) proteins, genes encoding HFGFs, methods for preparing HFGF proteins and therapeutic uses of HFGF proteins. The HFGF proteins of the present invention have a characteristic reduced expression in hair follicles derived from alopecia patients and have a stimulatory effect on hair follicle cell proliferation. HFGF proteins may be used to prevent or treat alopecia and to promote or accelerate hair growth and hair follicle repair.

40 Claims, 11 Drawing Sheets

OTHER PUBLICATIONS

Kay Ma et al., (1997) "Gene therapy" *Proc. Natl. Acad. Sci. USA* 94:12744-12746.

Jahoda Colin et al., (1996) "Dermal-Epidermal Interactions: Adult Follicle-Derived Cell Populations and Hair Growth" *Dermatologic Clinics* 14(4):573-583.

Peus D et al., (1996) "Growth Factors in Hair Organ Development and the Hair Growth Cycle" *Dermatologic Clinics* 14(4):559-572.

Ornitz et al., (1996) "Receptor Specificity of the Fibroblast Growth Factor Family" *The Journal of Biological Chemistry* 271(25):15292-15297.

Haskell RE et al., (1995) "Efficient Production of Transgenic Cattle by Retroviral Infection of Early Embryos" *Molecular Reproduction and Development* 40:386-390.

Connelly S et al., (1995) "*In Vivo* Gene Delivery and Expression of Physiological Levels of Functional Factor VIII in Mice" *Human Gene Therapy* 6:185-193.

Brandy DA et al., (1994) "Utilization of No-Kor Needles for Slit-Micrografting" *J Dermatol Surg Oncol* 20:336-339.

Jolly D, (1994) "Viral vector systems for gene therapy" *Cancer Gene Therapy* 1(1):51-64.

Kimura O et al., (1994) "Retroviral Delivery of DNA into the Livers of Transgenic Mice Bearing Premalignant and Malignant Hepatocellular Carcinomas" *Human Gene Therapy* 5:845-852.

Rossolini GM et al., (1994) "Use of deoxyinosine-containing primers vs degenerate primers for polymerase chain reaction based on ambiguous sequence information" *Molecular and Cellular Probles* 8:91-98.

Woffendin O et al., (1994) "Nonviral and viral delivery of a human immunodeficiency virus protective gene into primary human T cells" *Proc. Natl. Acad. Sci. USA* 91:11581-11585.

Kaplitt MG et al., (1994) "Long-term gene expression and phenotypic correction using adeno-associated virus vectors in the mammalian brain" *Nature Genetics* 8:148-153.

Philip R et al., (1994) "Efficient and Sustained Gene Expression in Primary T Lymphocytes and Primary and Cultured Tumor Cells Mediated by Adeno-Associated Virus Plasmid DNA Complexed to Cationic Liposomes" *Molecular and Cellular Biology* 14(4):2411-2418.

Curiel DT et al., (1992) "High-Efficiency Gene Transfer Mediated by Adenovirus Coupled to DNA-Polylysine Complexes" *Human Gene Therapy* 3:147-154.

Wall RJ et al., (1992) "Making Transgenic Livestock: Genetic Engineering on a Large Scale" *Journal of Cellular Biochemistry* 49:113-120.

Ford CF et al., (1991) "Fusion Tails for the Recovery and Purification of Recombinant Proteins" *Protein Expression and Purification* 2:95-107.

Batzer MA et al., (1991) "Enhanced evolutionary PCR using oligonucleotides with inosine at the 3'-terminus" *Nucleic Acids Research* 19(18):5081.

Miki T et al., (1991) "Expression cDNA Cloning of the KGF Receptor by Creation of a Transforming Autocrine Loop" *Science* 251:72-75.

Altschul SF et al., (1990) "Basic Local Alignment Search Tool" *J. Mol. Biol.* 215:403-410.

Sarkar G et al., (1990) "The "Megaprimer" Method of site-directed Mutagenesis" *BioTechniques* 8(4):404-407.

Cotsarelis G et al., (1990) "Label-Retaining Cells Reside in the Bulge Area of Pilosebaceous Unit: Implications for Follicular Stem Cells, Hair Cycle, and Skin Carcinogenesis" *Cell* 61:1329-1337.

Malardier L et al., (1989) "Cloning of the nitrate reductase gene (*niaD*) of *Aspergillus nidulans* and its use for transformation of *Fusarium oxysporum*" *Gene* 78:147-156.

Ho SN et al., (1989) "Site-directed mutagenesis by overlap extension using the polymerase chain reaction" *Gene* 77:51-59.

Wu CH et al., (1989) "Targeting Genes: Delivery and Persistent Expression of a Foreign Gene Driven by Mammalian Regulatory Elements *in vivo*" *The Journal of Biological Chemistry* 264(29):16985-16987.

Carrillo H et al., (1988) "The Multiple Sequence Alignment Problem In Biology" *Siam J. Appl. Math.* 48(5):1073-1083.

Cotton Richard GH et al., (1988) "Reactivity of cytosine and thymine in single-base-pair mismatches with hydroxylamine and osmium tetroxide and its application to the study of mutations" *Proc. Natl. Acad. Sci. USA* 85:4397-4401.

Grant FJ et al., (1987) "Improved RNA sequencing method to determine immunoglobulin mRNA sequence" *Nucleic Acids Research* 15(13):5496.

Stewart CL et al., (1987) "Expression of retroviral vectors in transgenic mice obtained by embryo infection" *The EMBO Journal* 6(2):383-388.

Cranage MP et al., (1986) "Identification of the human cytomegalovirus glycoprotein B gene and induction of neutralizing antibodies via its expression in recombinant vaccinia virus" *The EMBO Journal* 5(11):3057-3063.

Katsuoka et al. (1986) "Epidermal growth factor and fibroblast growth factor accelerate proliferation of human hair bulb papilla cells and root sheath fibroblasts cultured *in vitro*" *British Journal of Dermatology* 114(425):464-466.

Saiki RK et al., (1986) "Analysis of enzymatically amplified β-globin and HLA-DQα DNA with allele-specific oligonucleotide probes" *Nature* 324:163-166.

McKnight GL et al., (1985) "Identification and molecular analysis of a third *Aspergillus nidulans* alcohol dehydrogenase gene" *The EMBO Journal* 4(8):2093-2099.

Myers RM et al., (1985) "Detection of Single Base Substitutions by Ribonuclease Cleavage at Mismatches in RNA: DNA Duplexes" *Science* 230:1242-1246.

Jähner D et al., (1985) "Insertion of the bacterial *gpt* gene into the germ line of mice by retroviral infection" *Proc. Natl. Acad. Sci. USA* 82:6927-6931.

Putten H van Der et al., (1985) "Efficient insertion of genes into the mouse germ line via retroviral vectors" *Proc. Natl. Acad. Sci. USA* 82:6148-6152.

Ohtsuka E et al., (1985) "An Alternative Approach to Deoxyoligonucleotides as Hybridization Probes by Insertion of Deoxyinosine at Ambiguous Codon Positions" *The Journal of Biological Chemistry* 260(5):2605-2608.

Devereux J et al., (1984) "A comprehensive set of sequence analysis programs for the VAX" *Nucleic Acids Research* 12(1):387-395.

Stuhlmann H et al., (1984) "Introduction of a selectable gene into different animal tissue by a retrovirus recombinant vector" *Proc. Natl. Acad. Sci. USA* 81:7151-7155.

Yelton MM et al., (1984) "Transformation of *Aspergillus nidulans* by using a *trpC* plasmid" *Proc. Natl. Acad. Sci. USA* 81:1470-1474.

Ammerer Gustav, (1983) "Expression of Genes in Yeast Using the *ADCI* Promoter" *Methods In Enzymology* 101:192-201.

Palmiter RD et al., (1983) "Metallothionein-Human GH Fusion Genes Stimulate Growth of Mice" *Science* 222:809-814.

Russell DW et al., (1983) "DNA sequences of two yeast promoter-up mutants" *Nature* 304:652-655.

Gillies SD et al., (1983) "A Tissue-specific Transcription Enhancer Element is Located in the Major Intron of a Rearranged Immunoglobulin Heavy Chain Gene" *Cell* 33:717-728.

Simonsen CC et al., (1983) "Isolation and expression of an altered mouse dihydrofolate reductase cDNA" *Proc. Natl. Acad. Sci. USA* 80:2495-2499.

Russell PR, (1983) "Evolutionary divergence of the mRNA transcription initiation mechanism in yeast" *Nature* 301:167-169.

Kaufman RJ et al., (1982) "Construction of a Modular Dihydrofolate Reductase cDNA Gene: Analysis of Signals Utilized for Efficient Expression" *Molecular and Cellular Biology* 2(11):1304-1319.

Jähner D et al., (1982) "De *novo* methylation and expression of retroviral genomes during mouse embryogenesis" *Nature* 298:623-628.

Alber T et al., (1982) "Nucleotide Sequence of the Triose Phosphate Isomerase Gene of *Saccharomyces cerevisiae*" *Journal of Molecular and Applied Genetics* 1:419-434.

Southern PJ et al., (1982) "Transformation of Mammalian Cells to Antibiotic Resistance with a Bacterial Gene Under Control of the SV40 Early Region Promoter" *Journal of Molecular and Applied Genetics* 1:327-341.

Neumann E et al., (1982) "Gene transfer into mouse lyoma cells by electroporation in high electric fields" *The EMBO Journal* 1(7):841-845.

Young T et al., (1982) "The alcohol dehydrogenase genes of the yeast, *Saccharomyces cerevisiae*: isolation, structure, and regulation" *Basic Life Sci.* 19:335-361.

Corsaro CM et al., (1981) "Enhancing the Efficiency of DNA-Mediated Gene Transfer in Mammalian Cells" *Somatic Cell Genetics* 7(5):603-616.

DeNoto FM et al., (1981) "Human growth hormone DNA sequence and mRNA structure: possible alternative splicing" *Nucleic Acids Research* 9(15):3719-3730.

Subramani S et al., (1981) "Expression of the Mouse Dihydrofolate Reductase Complementary Deoxyribonucleic Acid in Simian Virus 40 Vectors" *Molecular and Cellular Biology* 1(9):854-864.

Ballou L et al., (1980) "*Saccharomyces cerevisiae* Mutants That Make Mannoproteins with a Truncated Carbohydrate Outer Chain" *The Journal of Biological Chemistry* 255(12):5986-5991.

Hitzeman RA et al., (1980) "Isolation and Characterization of the Yeast 3-Phosphoglycerokinase Gene (*PGK*) by an Immunological Screening Technique" *The Journal of Biological Chemistry* 255(24):12073-12080.

Botstein D et al., (1979) "Sterile Host Yeasts (SHY): A Eukaryotic System of Biological Containment For Recombinant DNA Experiments" *Gene* 8:17-24.

Broach JR et al., (1979) "Transformation in Yeast: Development of a Hybrid Cloning Vector and Isolation of the *CAN1* Gene" *Gene* 8:121-133.

Towbin H et al., (1979) "Electrophoretic transfer of proteins from polyacrylamide gels to nitrocellulose sheets: Procedure and some applications" *Proc. Natl. Acad. Sci. USA* 76(9):4350-4354.

Struhl K et al., (1979) "High-frequency transformation of yeast: Autonomous replication of hybrid DNA molecules" *Proc. Natl. Acad. Sci. USA* 76(3):1035-1039.

Wigler M et al., (1979) "DNA-mediated transfer of the adenine phosphoribosyltransferase locus into mammalian cells" *Proc. Natl. Acad. Sci. USA* 76(3):1373-1376.

Hutchinson CA et al., (1978) "Mutagenesis at a Specific Position in a DNA Sequence" *The Journal of Biological Chemistry* 253(18):6551-6560.

Beggs JD, (1978) "Transformation of yeast by a replicating hybrid plasmid" *Nature* 275:104-108.

Wigler M et al., (1978) "Biochemical Transfer of Single-Copy Eucaryotic Genes Using Total Cellular DNA as Donor" *Cell* 14:725-731.

Hinnen A et al., (1978) "Transformation of yeast" *Proc. Natl. Acad. Sci. USA* 75(4):1929-1933.

Jones EW, (1977) "Proteinase Mutants of *Saccharomyces cerevisiae*" *Genetics* 85:23-33.

Jaenisch R, (1976) "Germ line integration and Mendelian transmission of the exogenous Moloney leukemia virus" *Proc. Natl. Acad. Sci USA* 73(4):1260-1264.

Southern EM, (1975) "Detection of Specific Sequences Among DNA Fragments Separated by Gel Electrophoresis" *J. Mol. Biol.* 98:503-517.

Graham FL et al., (1973) "A New Technique for the Assay of Infectivity of Human Adenovirus 5 DNA" *Virology* 52:456-467.

Cohen SN et al., (1972) "Nonchromosomal Antibiotic Resistance in Bacteria: Gene Transformation of *Escherichia coli* by R-Factor DNA" *Proc. Natl. Acad. Sci. USA* 69(8):2110-2114.

Needleman SB et al., (1970) "A General Method Applicable to the Search for Similarities in the Amino Acid Sequences of Two Proteins" *J. Mol. Biol.* 48:443-453.

Figure 8

HFGF protein

| | |
|---|---|
| Met Trp Lys Trp Ile Leu Thr His Cys Ala Ser Ala Phe Pro His Leu | 16 |
| Pro Gly Cys Cys Cys Cys Cys Phe Leu Leu Leu Phe Leu Val Ser Ser | 32 |
| Val Pro Val Thr Cys Gln Ala Leu Gly Gln Asp Met Val Ser Pro Glu | 48 |
| Ala Thr Asn Ser Ser Ser Ser Ser Phe Ser Ser Pro Ser Ser Ala Gly | 64 |
| Arg His Val Arg Ser Tyr Asn His Leu Gln Gly Asp Val Arg Trp Arg | 80 |
| Lys Leu Phe Ser Phe Thr Glu Tyr Phe Leu Lys Ile Glu Lys Asn Gly | 96 |
| Lys Val Ser Gly Thr Lys Lys Glu Asn Cys Pro Tyr Ser Ile Leu Glu | 112 |
| Ile Thr Ser Val Glu Ile Gly Val Val Ala Val Lys Ala Ile Asn Ser | 128 |
| Asn Tyr Tyr Leu Ala Met Asn Lys Lys Gly Lys Leu Tyr Gly Ser Lys | 144 |
| Glu Phe Asn Asn Asp Cys Lys Leu Lys Glu Arg Ile Glu Glu Asn Gly | 160 |
| Tyr Asn Thr Tyr Ala Ser Phe Asn Trp Gln His Asn Gly Arg Gln Met | 176 |
| Tyr Val Ala Leu Asn Gly Lys Gly Ala Pro Arg Arg Gly Gln Lys Thr | 192 |
| Arg Arg Lys Asn Thr Ser Ala His Phe Leu Pro Met Val Val His Ser | 208 |

Figure 9

HFGF DNA sequence

```
atgtggaaat ggatactgac acattgtgcc tcagcctttc cccacctgcc
cggctgctgc tgctgctgct ttttgttgct gttcttggtg tcttccgtcc
ctgtcacctg ccaagccctt ggtcaggaca tggtgtcacc agaggccacc
aactcttctt cctcctcctt ctcctctcct tccagcgcgg gaaggcatgt
gcggagctac aatcaccttc aaggagatgt ccgctggaga aagctattct
ctttcaccga gtactttctc aagattgaga agaacgggaa ggtcagcggg
accaagaagg agaactgccc gtacagcatc ctggagataa catcagtaga
aatcggagtt gttgccgtca aagccattaa cagcaactat tacttagcca
tgaacaagaa ggggaaactc tatggctcaa aagaatttaa caatgactgt
aagctgaagg agaggataga ggaaaatgga tacaatacct atgcatcatt
taactggcag cataatggga ggcaaatgta tgtggcattg aatggaaaag
gagctccaag gagaggacag aaaacacgaa ggaaaaacac ctctgctcac
tttcttccaa tggtggtaca ctcatag
```

HAIR FOLLICLE GROWTH FACTOR PROTEINS

RELATED APPLICATIONS

The present application claims priority to Korean Application 10-2001-0028621, filed May 24, 2001, which is hereby incorporated by reference in their entireties.

FIELD OF THE INVENTION

The present invention relates to newly isolated hair follicle growth factor (HFGF) proteins, genes encoding HFGF proteins, methods of preparing HFGF proteins and genes encoding the same, and therapeutic or diagnostic uses thereof. More specifically, the present invention relates to HFGF proteins which are newly isolated from hair follicles of human scalp skin, genes encoding said HFGF proteins, expression vectors containing said gene, host cells transformed with said vector, and methods for recombinantly producing HFGF proteins and genes encoding the same. HFGF proteins of the present invention have reduced expression in hair follicles derived from alopecia patients and exhibit a stimulatory effect on hair follicle cell proliferation. HFGF proteins and genes encoding the same are useful in prevention or treatment of alopecia and in promotion, acceleration or induction of hair growth and hair follicle repair. In addition, HFGF proteins and genes encoding the same can be applied for hair transplantation in alopecia patients. Moreover, HFGF proteins and genes encoding the same can be used to diagnose alopecia symptoms.

BACKGROUND OF THE INVENTION

The hair follicle is an epidermal derivative that undergoes cycles of growth (anagen), involution (catagen), and rest (telogen). Although the mechanisms underlying hair cycling have not been fully elucidated, the core of the process involves interactions between the mesenchymal and epithelial cell populations within the hair follicle unit (Jahoda, C. A. & Reynolds, A. J. (1996) Dermatol. Clin. 14, 573–583). The most obvious regulator of the cycle is the papillary mesenchyme, in particular the dermal papilla.

Factors from the papillary mesenchyme act as inductive signals for cycling of the follicular epithelium (Peus, D. & Pittelkow, M. R. (1996) Dermatol. Clin. 14, 559–572). In particular, it has been inferred that epithelial stem cells, which reside in the bulge area of the hair follicles, can respond to the inductive signals from the dermal papilla and become activated (Cotsarelis, G., Sun, T. T. & Lavker, R. M. (1990) Cell 61, 1329–1337). This activation leads to proliferation of stem cells in the bulge area, and then the stem cell progeny forms a downgrowth into the deep dermis, followed by differentiative growth of matrix cells and generation of the complex follicular product, the shaft, and its housing sheath.

Analyses of the skin phenotypes of a considerable number of transgenic or gene knockout mice have shed light on the mesenchymal (dermal papilla) and epithelial (keratinocyte) interactions involved in the morphogenesis of hair follicles in the fetus (Gat, U. et al. (1998) Cell 95, 605–614; Chiang, C. et al. (1999) Dev. Biol. 205, 1–9; Botchkarev, V. A. et al. (1999) Nat. Cell Biol. 1, 158–164). The mechanisms underlying the biological switching process in postnatal follicles occurring between telogen and anagen, however, have remained unclear. The most likely candidate for factors inducing such switching is KGF-2, because KGF-2 is found in dermal papilla fibroblasts and its receptor, FGFR2IIIb, is found in neighboring keratinocytes (Katsuoka K., Schell H., Hornstein O. P., Wessel B. (1987) Br. J. Dermatol Mar 116(3), 464–5).

The kgf-2 (fgf-10) gene is a member of the fibroblast growth factor (referred to hereinfter as "FGF") gene family comprising more than 22 genes in mammals (Nishimura T., Nakatake Y., Konishi M., Itoh N. (2000) Biochim. Biophys. Acta. 1492, 203–206). The FGF proteins are thought to regulate cellular proliferation, differentiation, migration, and survival by binding to and activating members of a family of tyrosine kinase receptors, i.e. FGF receptors (FGFRs). Among the 22 known FGF proteins, KGF-2 is structurally most related to FGF-7 (Miki T. et al. (1991) Science 251, 72–75 ; Ornitz D. M. et al. (1996) J. Biol. Chem. 271, 15292–15297 ; Igarashi M. et al. (1998) J. Biol. Chem. 273, 13230–13235), and both FGFs specifically bind to one isoform out of four FGFRs, i.e. FGFR2IIIb (Miki T. et al. (1991) Science 251, 72–75 ; Ornitz D. M. et al. (1996) J. Biol. Chem. 271, 15292–15297 ; Igarashi M. et al. (1998) J. Biol. Chem. 273, 13230–13235).

Functionally, KGF-2 has been shown to be involved in outgrowth of the limb bud and branching morphogenesis of the lung (Martin G. R. (1998) Genes Dev. 12, 1571–15869). The limb and lung buds are typical examples of organprimordia, which require intimate epithelial-mesenchymal interactions during development.

In epithelial-mesenchymal interactions, signals from the mesenchyme direct epithelial components to generate specific structures through budding or branching morphogenesis, and reciprocal interactions between the two tissues must be maintained during further development.

U.S. Pat. Nos. 5,184,605, 5,824,643 and 5,965,530 discuss the role of KGF-1 in the stimulation of proliferation, growth and differentiation in various cells of epithelial tissue, besides keratinocytes. It is thought that KGF-1 may be used as a therapeutic agent for the specific treatment of disease states and medical conditions afflicting tissues and organs such as the dermal adnexae, the liver, the lung and the gastrointestinal tract. The dermal adnexae include sebaceous glands, sweat glands and hair follicles.

The re-epithelialization activity of KGF has only been observed in dermis having an induced wound. The use of KGF for treatment of inherited alopecia is not taught or suggested by any of the above references.

Ruben et al., U.S. Pat. No. 6,077,692, disclose a newly identified KGF-2 which exhibits biological activities such as wound healing, anti-inflammatory effects, stimulation of differentiation and proliferation of liver cells and protection against lung damage. However, there is no experimental data regarding the effect of KGF-2 on the proliferation of hair follicle cells.

SUMMARY OF THE INVENTION

The present inventors have undertaken studies in an attempt to isolate a molecular factor for treating alopecia and have developed hair follicle growth factor (HFGF) proteins from human hair follicle, which have a reduced expression in hair follicles derived from alopecia patients and show stimulatory effects on hair follicle cell proliferation. The amino acid sequence of HFGF protein (SEQ ID NO: 1) is provided in FIG. 8. HFGF is considered to be an allelic form of keratinocyte growth factor-2 (KGF-2) wherein HFGF has a glutamic acid residue (Glu) at position 87, whereas KGF-2 has a lysine residue (Lys) at this position.

In one aspect, the present invention provides an isolated polypeptide having the amino acid sequence of Ser 69 to Ser 208 of SEQ ID NO:1 or an isolated polypeptide comprising the amino acid sequence of Ser 69 to Ser 208 of SEQ ID NO:1, wherein Glu 87 is replaced by Asp 87.

In another aspect, the present invention provides an isolated nucleic acid molecule comprising a nucleotide sequence encoding the amino acid sequence of Ser 69 to Ser 208 of SEQ ID NO: 1 or an isolated nucleic acid molecule comprising a nucleotide sequence encoding the amino acid sequence of Ser 69 to Ser 208 of SEQ ID NO: 1, wherein Glu 87 is replaced by Asp 87.

In other aspect, the present invention provides a vector comprising the nucleic acid encoding the amino acid sequence of Ser 69 to Ser 208 of SEQ ID NO: 1 or the amino acid sequence of Ser 69 to Ser 208 of SEQ ID NO: 1, wherein Glu 87 is replaced by Asp 87.

In still other aspect, the present invention provides a host cell transfected with the vector comprising a transcription promoter, a DNA encoding the amino acid sequence of Ser 69 to Ser 208 of SEQ ID NO: 1 or the amino acid sequence of Ser 69 to Ser 208 of SEQ ID NO: 1, wherein Glu 87 is replaced by Asp 87, and a transcription terminator, wherein said promoter is operably linked to the DNA segment, and the DNA segment is operably linked to the transcription terminator.

In a further aspect, the present invention provides a method of producing a polypeptide comprising an amino acid sequence of Ser 69 to Ser 208 of SEQ ID NO: 1 which comprises culturing a host cell under conditions such that said polypeptide is expressed, and isolating said polypeptide from the cultures, wherein said host cell is transfected with the vector comprising a transcription promoter, a DNA encoding the amino acid sequence of Ser 69 to Ser 208 of SEQ ID NO: 1, and a transcription terminator, said promoter being operably linked to the DNA, and the DNA being operably linked to the transcription terminator. Also, the present invention provides a method of producing an isolated polypeptide comprising an amino acid sequence of Ser 69 to Ser 208 of SEQ ID NO: 1, wherein Glu 87 is replaced by Asp 87, which comprises culturing a host cell under conditions such that said polypeptide is expressed and isolating said polypeptide from the cultures, wherein said host cell is transfected with the vector comprising a transcription promoter, a nucleic acid encoding the amino acid sequence of Ser 69 to Ser 208 of SEQ ID NO: 1, wherein Glu 87 is replaced by Asp 87, and a transcription terminator, said promoter being operably linked to the DNA, and the DNA being operably linked to the transcription terminator.

In an additional aspect, the present invention provides a pharmaceutical composition comprising the polypeptide which comprises an amino acid sequence of Ser 69 to Ser 208 of SEQ ID NO: 1 or an amino acid sequence of Ser 69 to Ser 208 of SEQ ID NO: 1 wherein Glu 87 is replaced by Asp 87, and a pharmaceutically acceptable carrier.

In still another aspect, the present invention provides a pharmaceutical composition comprising the nucleic acid molecule which comprises the nucleotide sequence encoding the amino acid sequence of Ser 69 to Ser 208 of SEQ ID NO: 1 or the nucleotide sequence encoding an amino acid sequence of Ser 69 to Ser 208 of SEQ ID NO: 1, wherein Glu 87 is replaced by Asp 87, and a pharmaceutically acceptable carrier.

In still another aspect, the present invention provides a method for treating, preventing or ameliorating alopecia in a subject, which comprises administering the composition containing the polypeptide comprising an amino acid sequence of Ser 69 to Ser 208 of SEQ ID NO: 1 or the polypeptide comprising an amino acid sequence of Ser 69 to Ser 208 of SEQ ID NO: 1, wherein Glu 87 is replaced by Asp 87, and a pharmaceutically acceptable carrier, to said subject.

In still another aspect, the present invention provides a method for treating, preventing or ameliorating alopecia in a subject, which comprises administering the composition containing the nucleic acid molecule encoding an amino acid sequence of Ser 69 to Ser 208 of SEQ ID NO: 1 or the nucleic acid molecule encoding an amino acid sequence of Ser 69 to Ser 208 of SEQ ID NO: 1 wherein Glu 87 is replaced by Asp 87, and a pharmaceutically acceptable carrier, to said subject.

In another aspect, the present invention provides a method for stimulating, accelerating or inducing hair growth or hair follicle repair in a subject, which comprises administering the composition containing the polypeptide comprising an amino acid sequence of Ser 69 to Ser 208 of SEQ ID NO: 1 or the polypeptide comprising an amino acid sequence of Ser 69 to Ser 208 of SEQ ID NO: 1 wherein Glu 87 is replaced by Asp 87, and a pharmaceutically acceptable carrier to said subject.

In another aspect, the present invention provides a method for stimulating, accelerating or inducing hair growth or hair follicle repair in a subject which comprises administering the composition containing the nucleic acid molecule encoding an amino acid sequence of Ser 69 to Ser 208 of SEQ ID NO: 1 or the nucleic acid molecule encoding an amino acid sequence of Ser 69 to Ser 208 of SEQ ID NO: 1 wherein Glu 87 is replaced by Asp 87, and a pharmaceutically acceptable carrier, to said subject.

In another aspect, the present invention provides a method for transplanting hair in a subject which comprises supplementing scalp hair follicles or grafts with the polypeptide comprising an amino acid sequence of Ser 69 to Ser 208 of SEQ ID NO: 1 or the polypeptide comprising an amino acid sequence of Ser 69 to Ser 208 of SEQ ID NO: 1, wherein Glu 87 is replaced by Asp 87 and transplanting the supplemented hair grafts or follicles with the polypeptide to the bald or thinning area of said subject. Also, the present invention provides a method for transplanting hair in a subject which comprises supplementing scalp hair follicles or grafts with the nucleic acid molecule encoding an amino acid sequence of Ser 69 to Ser 208 of SEQ If NO: 1 or the nucleic acid molecule encoding an amino acid sequence of Ser 69 to Ser 208 of SEQ ID NO: 1, wherein Glu 87 is replaced by Asp 87.

In another aspect, the present invention provides a method for diagnosing alopecia in a subject comprising collecting a blood or tissue sample from said subject and detecting HFGF proteins in said sample.

BRIEF DESCRIPTION OF THE DRAWINGS

The foregoing summary, as well as the following detailed description of the invention, will be better understood when read in conjunction with the appended drawings. For the purpose of illustrating the invention, the drawings exhibit embodiment(s) which are presently preferred. It should be understood, however, that the invention is not limited to the precise arrangements and instrumentalities shown.

FIG. 8 shows the amino acid sequence of hair follicle growth factor (HFGF) (SEQ ID NO:1).

FIG. 9 shows that nucleic acid sequence encoding hair follicle growth factor (HFGF) (SEQ ID NO:2).

DETAILED DESCRIPTION OF THE INVENTION

Figure 1:
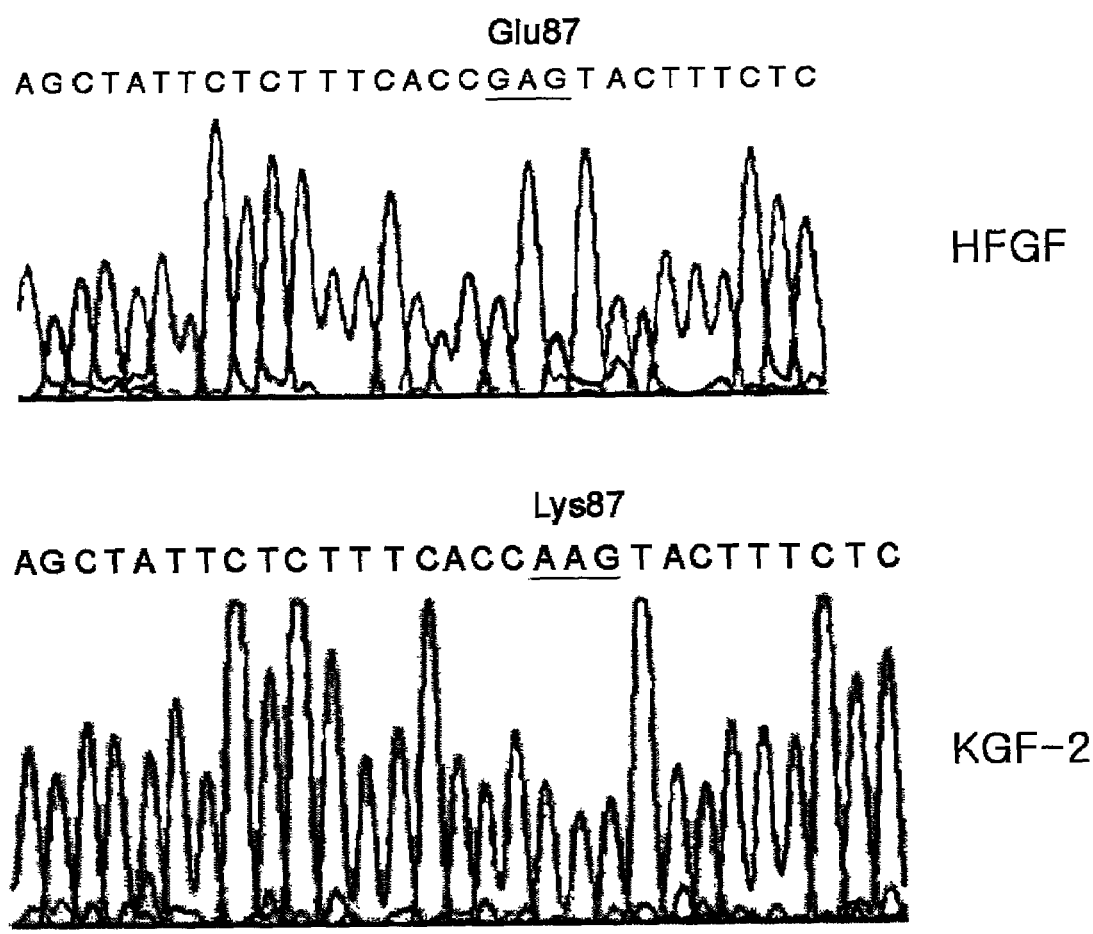
FIG. 1 shows a nucleotide and amino acid sequence comparison between human HFGF of the present invention and known human KGF-2.

The full amino acid sequence and nucleotide sequence of Keratinocyte Growth Factor-2 (KGF-2) are known in the art. The polypeptide of the present invention shown in SEQ ID NO: 1 has an amino acid sequence containing a glutamic acid residue at position 87, instead of a lysine residue at position 87. This polypeptide was designated Hair Follicle Growth Factor and is referred to herein as HFGF or HFGF protein. HFGF has a characteristic reduced expression in hair follicles derived from alopecia patients and shows a stimulatory effect on hair follicle cell proliferation. According to the present invention, an amino acid sequence of Ser 69 to Ser 208 having a glutamic acid residue at position 87 as shown in SEQ ID NO: 1 is found to be important to effecting hair follicle cell proliferation. The polypeptides comprising at least an amino acid sequence of Ser 69 to Ser 208 of SEQ ID NO: 1 are nearly equal to HFGF in their stimulatory activity on hair follicle cell proliferation. In particular, the amino acid residue at position 89, i.e., glutamic acid (Glu 89), is found to have a strong influence on hair follicle cell proliferation. Accordingly, the polypeptides of the present invention include the polypeptides further comprising at least one contiguous sequence of amino acids Met 1 to Ala 39 of SEQ ID NO: 1 at the N-terminus of said polypeptide. In addition, the polypeptides of the present invention include the polypeptides having substitutions, deletions and/or insertions of one, two, three, four or more amino acid residues in the region of Met 1 to Ala 39 of SEQ ID NO: 1.

The polypeptides according to the present invention include another group of polypeptides comprising an amino acid sequence in glutamic acid at position 37 is replaced by aspartic acid (Asp). Likewise, this group of the polypeptides having an aspartic acid residue at position 87 includes the polypeptides further comprising at least one contiguous sequence of amino acids Met 1 to Ala 39 of SEQ ID NO: 1 at the N-terminus of said polypeptide and the polypeptides having substitutions, deletions and/or insertions of one, two, three, four or more amino acid residues in the region of Met 1 to Ala 39 of SEQ ID NO: 1. As with Glu 87, Asp 87 plays an important role in proliferation of hair follicle cells.

The isolated polypeptides as defined above are sometimes collectively referred to herein as "HFGF proteins". Therefore, examples of HFGF proteins are the polypeptide having Met 1 to Ser 208 of the amino acid sequence shown in SEQ ID NO: 1, the polypeptide having Leu 40 to Ser 208 of the amino acid sequence shown in SEQ ID NO: 1, and the polypeptide having Ser 69 to Ser 208 of the amino acid sequence shown in SEQ ID NO: 1.

Additionally, the polypeptides of the present invention may further comprise a Met residue at the N-terminus of any of said amino acid sequences. Moreover, the polypeptides of the present invention may be mature proteins. These polypeptides are also included in HFGF proteins of the present invention.

In the broadest aspect, the present invention therefore provides an isolated polypeptide comprising an amino acid sequence of Ser 69 to Ser 208 of SEQ ID NO: 1 or an isolated polypeptide comprising an amino acid sequence of Ser 69 to Ser 208 of SEQ ID NO: 1 wherein Glu 87 is replaced by Asp 87.

In one embodiment, the present invention is directed to a HFGF that is newly isolated from hair follicles of human scalp skin and is a variant or allelic form of known KGF-2. To isolate HFGF of the present invention from hair follicles of human scalp skin, total mRNA was extracted from hair follicles and cDNA was obtained from total RNA by performing RT-PCR (Reverse Transcriptase-Polymerase Chain Reaction). After the nucleotide sequences of cDNA produced by the above RT-PCR were identified, the amino acid sequences corresponding to the nucleotide sequences of said cDNA were deduced and determined. One of the deduced amino acid sequences was identified as an amino acid sequence wherein glutamic acid replaces lysine at position 87 of the KGF-2 protein. The amino acid sequence of HFGF protein is shown in SEQ ID NO: 1.

In another embodiment, the present invention is directed to a variant or allelic form of HFGF wherein Asp 87 replaces Glu 87. It was found by the inventors that a negatively charged amino acid at position 87 of KGF-2 increases the hair follicle cell proliferation activity in comparison to wild type KGF-2.

The HFGF proteins of the present invention can be readily made by a conventional recombinant DNA technique. The coding region for HFGF proteins can be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2nd Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.). Polymerase chain reaction (PCR) can be used to amplify DNA sequences encoding HFGF proteins in a genomic or cDNA library. Synthetic oligonucleotides may be utilized as primers to amplify by PCR sequences from a source (RNA or DNA), preferably a cDNA library. The DNA being amplified can include cDNA or genomic DNA from any human. After successful isolation or amplification of a segment of HFGF, that segment may be molecularly cloned and sequenced, and utilized as a probe to isolate a complete cDNA or genomic clone.

Alternatives to isolating the coding regions for HFGF proteins include, but are not limited to, chemically synthesizing the gene sequence itself from the proposed sequence. Other methods are possible and within the scope of the invention. The above methods are not meant to limit the following general description of methods by which HFGF proteins can be obtained.

The identified and isolated gene can be inserted into an appropriate cloning vector for amplification of the gene sequence. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR 322 or pUC plasmid derivatives or the BLUESCRIPT vector (Stratagene). The insertion into a cloning vector can, for example, be accomplished by ligating the DNA fragment into a cloning vector which has complementary cohesive termini. However, if the complementary restriction sites to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment of the desired gene, for example, by size fractionation, can be done before insertion into the cloning vector.

In specific embodiments, transformation of host cells with recombinant DNA molecules that comprise the gene encoding HFGF protein, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA. Copies of the gene are used in mutagenesis experiments to study the structure and function of HFGF proteins.

The mutations present in HFGF proteins of the present invention can be produced by various methods known in the art. The manipulations which result in their production can be produced at the gene or protein level. For example, the cloned coding region of the KGF-2 protein can be modified by any of numerous strategies known in the art (Sambrook et al., 1990, Molecular Cloning, A Laboratory Manual, 2nd. Ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. Additionally, the nucleic acid sequences encoding the HFGF proteins can be mutated in vitro or in vivo, to create variations in desired coding regions (e.g., amino acid residue 87 substitution), and/or to create and/or destroy translation initiation, and/or termination sequences, and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), PCR-based overlap extension (Ho et al., 1989, Gene 77:51–59), PCR-based megaprimer mutagenesis (Sarkar et al., 1990, Biotechniques, 8:404–407), etc. Mutations can be confirmed by double stranded dideoxy DNA sequencing.

Manipulations of the mutant sequence may also be made at the protein level. Included within the scope of the invention are HFGF proteins which are differentially modified during or after translation, e.g., by glycosylation, acetylation, phosphorylation, amidation, derivatization by known protecting/blocking groups, proteolytic cleavage, linkage to another cellular ligand, etc. Any of numerous chemical modifications may be carried out by known techniques, including but not limited to specific chemical cleavage by cyanogen bromide, trypsin, chymotrypsin, papain, V8 protease or $NaBH_4$, acetylation, formylation, oxidation, reduction, metabolic synthesis in the presence of tunicamycin, etc.

In a specific embodiment, HFGF of the present invention was isolated from hair follicles of human scalp skin and showed a different level of expression in hair follicles of alopecia patients in comparison to hair follicles of persons that do not have alopecia. To investigate the expression level of HFGF, hair follicles with a morphological structure characteristic of anagen were obtained from human scalp skin of alopecia patients and persons that do not have alopecia. Total mRNA was then extracted from said hair follicles and cDNA was obtained from the total RNA by RT-PCR and analyzed on agarose gels.

The results of agarose gel analysis showed that cDNA encoding HFGF was detected in persons that do not have alopecia while cDNA corresponding to mRNA encoding HFGF in alopecia patients was not detected. In contrast, cDNA of HFGF receptor was detected in both (see FIG. 3), demonstrating that HFGF may be a molecular factor that regulates hair loss.

In another specific embodiment, the present invention also provides a gene or isolated nucleic acid molecule encoding HFGF protein (herein referred to as "HFGF gene"). A HFGF gene encodes a protein having the $2^{nd}$ to the $208^{th}$ amino acids of SEQ ID NO:1, wherein lysine 87 is replaced by glutamic acid. The HFGF gene may further comprise an initiation codon at the 5'-end of said gene.

In additional specific embodiment, mutant HFGF genes of the present invention may comprise the $4^{th}$ to the $627^{th}$ nucleotides or the $118^{th}$ to the $627^{th}$ nucleotides of SEQ ID NO: 2, wherein the codon corresponding to the amino acid at position 87 of the amino acid sequence encodes negatively charged amino acid, i.e., glutamic acid or aspartic acid. These mutants may further comprise an initiation codon at the 5'-end of said nucleotide sequences.

The present invention provides methods for producing HFGF proteins. Methods of the present invention include subcloning, for example, HFGF gene into a vector, transforming host cells with said vector and culturing said transformants, wherein said HFGF gene encodes the $2^{nd}$ to the $208^{th}$ amino acids of SEQ ID NO:1, and may further comprise an initiation codon at the 5'-end of the nucleic acid sequences. A HFGF gene of the present invention may be a gene fusion in which additional nucleotide sequences are joined to a HFGF gene.

The present invention also provides pharmaceutical compositions containing HFGF proteins, or genes encoding said proteins, as an active component. A specific embodiment uses IFGF comprising the 2nd to the 208th amino acids of SEQ ID NO:1. In another specific embodiment, the pharmaceutical composition of the present invention contains HFGF protein comprising the 40th to the 208th amino acids of SEQ ID NO:1 or a gene encoding said analogue. In further specific embodiment, the pharmaceutical composition contains another HFGF protein having the 69th to the 208th amino acids of SEQ ID NO:1. In additional embodiments, the pharmaceutical composition of the present invention contains HFGF protein comprising the 2nd to the 208th amino acids of SEQ ID NO:1, wherein Asp 87 is replaced by Glu 87, the 40th to the 208th amino acids of SEQ ID NO:1, wherein Asp 87 is replaced by Glu 87, 69th to the 208th amino acids of SEQ ID NO:1, wherein Asp 87 is replaced by Glu 87 or genes encoding said proteins.

The pharmaceutical compositions of the present invention are useful for preventing or treating alopecia and for promoting or accelerating hair growth and hair follicle repair. In a specific embodiment, the present invention provides methods of using HFGF or HFGF gene to prevent or treat or ameliorate alopecia, comprising administering a pharmaceutical composition containing HFGF or HFGF gene as an effective component to a patient in need thereof.

Another aspect of the present invention is a HFGF gene encoding HFGF protein. A HFGF gene may be constituted of all possible degenerate sequences encoding said amino acid sequence. Furthermore, a HFGF gene may be in the form of cDNA or gDNA (genomic DNA), and it may comprise non-coding regions such as introns, promoters and/or enhancers. In one preferred embodiment of the invention, mutant HFGF genes encode the 2nd to the 208th amino acids, the 40th to the 208th amino acids or the 69th to the 208th of SEQ ID NO:1, wherein the amino acid residue at position 87 is glutamic acid or aspartic acid, and may further comprise an initiation codon at the 5'-end the nucleotide sequences.

In another preferred embodiment, mutant HFGF genes of the present invention comprise the 4th to the 627th or the 118th to the 627th nucleotides of SEQ ID NO: 2, wherein the codon corresponding to the amino acid at position 87 of the amino acid sequence encodes glutamic acid or aspartic acid, and may further comprise an initiation codon at the 5'-end of the nucleotide sequences. Of course, it would be routine for those skilled in the art to generate variants of the above nucleotide sequences by virtue of the degeneracy of the genetic code. Degenerate variants of the disclosed nucleic acid sequences are an aspect of the present invention.

In a specific embodiment to obtain a HFGF gene of the present invention, total RNA was extracted from hair follicle cells. As generally known to those of skill in the art, total RNA derived from a cell can be converted to cDNA by PCR or RT-PCR using oligonucleotide primers corresponding to specific nucleotide sequences of the gene or nucleic acid sequence intended to be amplified.

In this regard, oligonucleotide primers shown as SEQ ID NO: 3 and SEQ ID NO: 4 were utilized to amplify a HFGF gene comprising the 1st to the 627th nucleotides of SEQ ID NO: 2, and oligonucleotide primers shown as SEQ ID NO: 9 and SEQ ID NO: 10 were used to amplify a HFGF gene comprising the 118th to the 627th nucleotides of SEQ ID NO: 2.

In one embodiment, total RNA extracted from hair follicle cells was used as template to perform PCR with oligonucleotide primers shown as SEQ ID NO: 3 and SEQ ID NO: 4. The nucleotide sequence of a PCR product was identified, which provides a new cDNA sequence in which Glu is substituted for Lys at the 87th codon of that of human kgf-2 gene (see FIG. 1 and SEQ ID NO:2).

The gene, newly isolated by the above process and referred to as HFGF gene, was inserted into the pGEM-T vector to construct a recombinant plasmid which can express HFGF of the present invention in a host cell. The construct was designated pGEM-T-KFG-2A and deposited in Korean Collection for Type Cultures which is an international depository authority under the regulations of Budapest Treaty on the International Recognition of the Deposit of Microorganisms for the Purpose of Patent Procedures, on Mar. 19, 2001 as Accession No. KCTC-1012BP.

In a further aspect, the present invention provides a method for producing HFGF. In one embodiment, HFGF may be produced by direct synthetic processes to yield a protein corresponding to the amino acid sequence of SEQ ID NO:1. In another embodiment, HFGF may be isolated from hair follicles of human scalp skin. In still another embodiment, HFGF may be prepared by recombinant expression using a HFGF gene.

In a specific embodiment of the invention, HFGF is produced by subcloning a HFGF gene into a vector, transforming a host cell with said vector and culturing said transformant, wherein said HFGF gene encodes the 2nd to the 208th amino acids or the 40th to the 208th amino acids of SEQ ID NO:1, and may further comprise an initiation codon at the 5'-end of the nucleic acid sequences. A HFGF gene of the present invention may be a gene fusion in which additional nucleotide sequences are joined to a HFGF gene.

Examples of additional nucleotide sequences that may be fused to a HFGF gene sequence include sequences encoding signals (such as secretion signal sequences) for protein transport following protein expression, membrane anchor sequences, immunogenic determinants, tags, such as Histidine tags for aiding in the isolation or purification of protein; glutathione-S-transferase, and enzyme-specific restriction sequences etc. The additional sequences may be cut or removed after expression or purification of protein.

In one embodiment, a recombinant plasmid may be constructed by subcloning a HFGF gene into a commercial expression vector such as pET9c or pGEX-2T. The pET9c vector contains a T7 promoter for inducing high level expression of a target gene. The pGEX-2T vector contains a GST (Glutathione S Transferase)-encoding sequence upstream of the insertion site for a target gene, which results in expression of GST-fusion protein.

In one embodiment, a pGEX-2T-HFGF recombinant plasmid was constructed by subcloning a HFGF gene into the pGEX-2T vector, wherein said HFGF gene comprised the 118th to the 627th nucleotides of SEQ ID NO:2 wherein the sequence lacked the 1st to the 117th nucleotides encoding a signal sequence.

A transformant of the present invention may be prepared by transforming prokaryotic or eukaryotic host cells such as E. coli or yeast with a recombinant plasmid containing HFGF gene using well-known methodology, e.g. calcium chloride mediated transformation, calcium-phosphate precipitation, liposome mediation, microinjection, transfection by electroporation, etc.

In a preferred embodiment of the invention, E. coli strain BL21(DE3) is utilized as a host cell, that is, E. coli BL21 (DE3) is transformed with a pGEX-2T-HFGF vector.

Generally, to isolate and purify protein from a transformant, the transformant is cultured for an appropriate time and then lysed. Subsequently, selective precipitation, chromatography, dialysis and/or filtration may be performed to purify the desired protein.

731 In a preferred embodiment of the invention, the above E. coli BL21(DE3) containing pGEX-2T-HFGF vector was cultured for 48 hours or more and lysed. Said cell lysate was then applied to a heparin-Sepharose column, hHFGF was eluted with a concentration-gradient using NaCl solutions and purified.

If a host cell transformed with pGEX-2T-HFGF vector is cultured, a GST-HFGF fusion protein is expressed. In this case, said fusion protein may be specifically purified using glutathione column chromatography. The GST moiety may be removed from the target protein by thrombin treatment. The selection and application of a suitable column for isolation and purification of protein will be appreciated by those skilled in the art.

In the case of subcloning a fused gene composed of a HFGF gene fused with additional nucleotide sequences into an expression vector, amino acids encoded by the additional nucleotides may be cut or removed from HFGF by using enzymes such as trypsin, or any other endopeptidase or endoprotease, after expression of the fusion protein.

Figure 2:
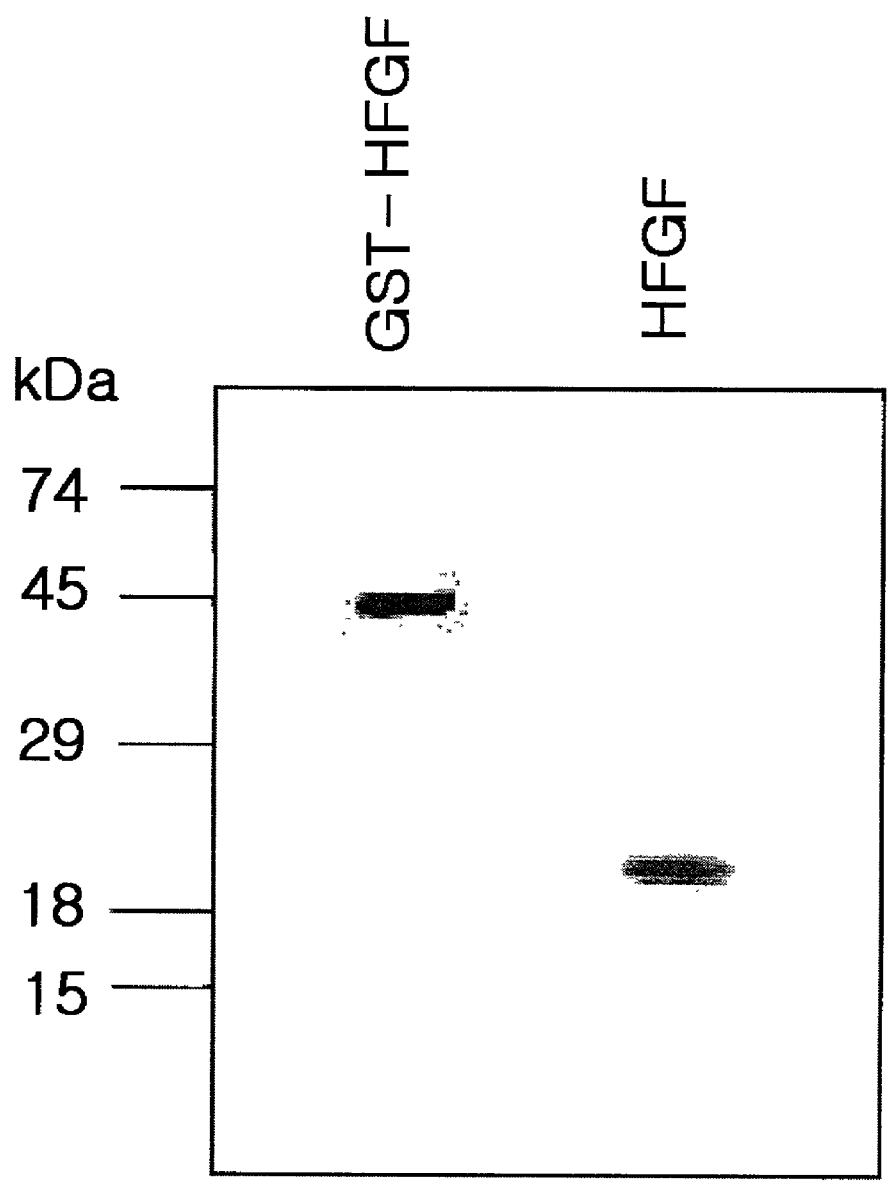
FIG. 2 is a photograph of an SDS-polyacrylamide electrophoresis gel (SDS-PAGE) showing the molecular mass of GST-HFGF and HFGF prepared by a method of the present invention.

The apparent molecular mass of HFGF determined by polyacrylaminde gel electrophoresis (PAGE) was approximately 20 kDa and that of a GST-HFGF fusion protein was approximately 45 kDa, consistent with the predicted molecular weights (see FIG. 2).

In another aspect, the present invention is also directed to pharmaceutical compositions containing HFGF, or a gene encoding a HFGF, as an effective component, wherein said HFGF comprises the $2^{nd}$ to the $208^{th}$ amino acids or the $40^{th}$ to the $208^{th}$ amino acids of SEQ ID NO: 1, and may further comprise a Met residue at the N-terminus of said amino acid sequences, wherein said HFGF may be mature protein.

Furthermore, a HFGF gene of the present invention encodes the 2nd to the $208^{th}$ amino acids or the $40^{th}$ to the $208^{th}$ amino acids of SEQ ID NO:1, and may further comprise an initiation codon at the 5'-end of the nucleic acid sequence, and said HFGF gene may be a fused gene bound to additional nucleotide sequences.

Mitogenic activity of HFGF on human hair follicles was measured to investigate the biological activities of HFGF. Particularly, HFGF was used to treat hair follicle cells from human scalp skin, and after a period of about 48 hours, cell proliferation was measured by colorimetric MTS assays.

Figure 5:
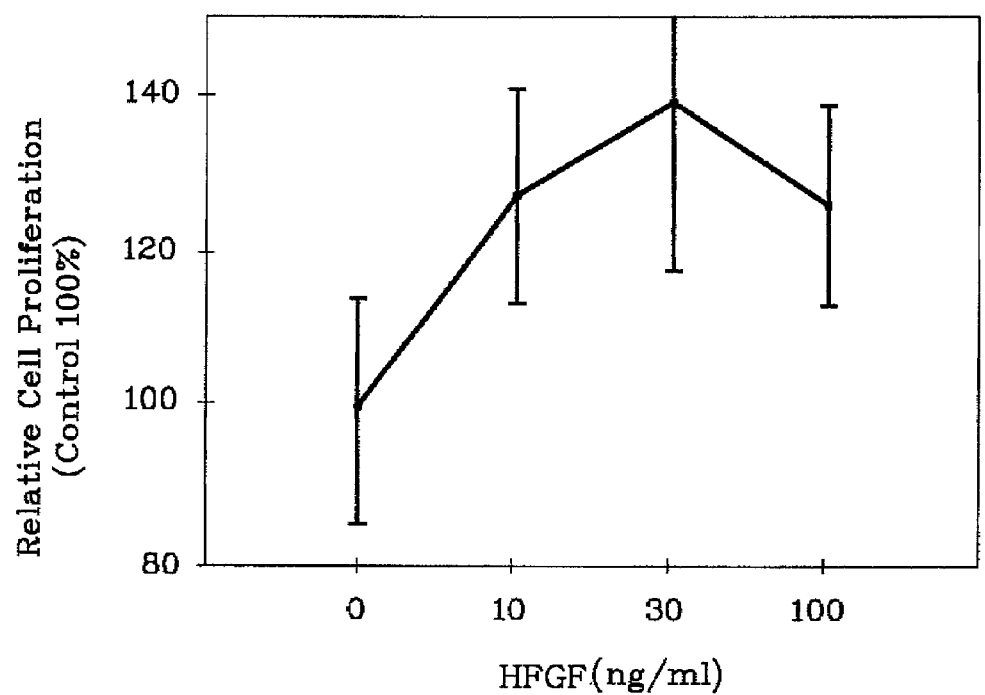
FIG. 5 is a graph showing the stimulatory activity of HFGF protein on hair follicle cell proliferation identified by calorimetric MTS assays.

Accordingly, as seen in FIG. 5, the addition of HFGF resulted in a dose-dependent stimulation of proliferation of human hair follicle cells with a maximum stimulatory effect observed at a HFGF concentration of 30 ng/ml; with an increased effect of 140% compared to negative control of 100%.

To exclude any effect caused by endogenous KGF-2, HFGF was used to treat human hair follicles in which dermal papilla (DP) were removed surgically. Cell proliferation was measured by calorimetric MTS assay.

Figure 6A:
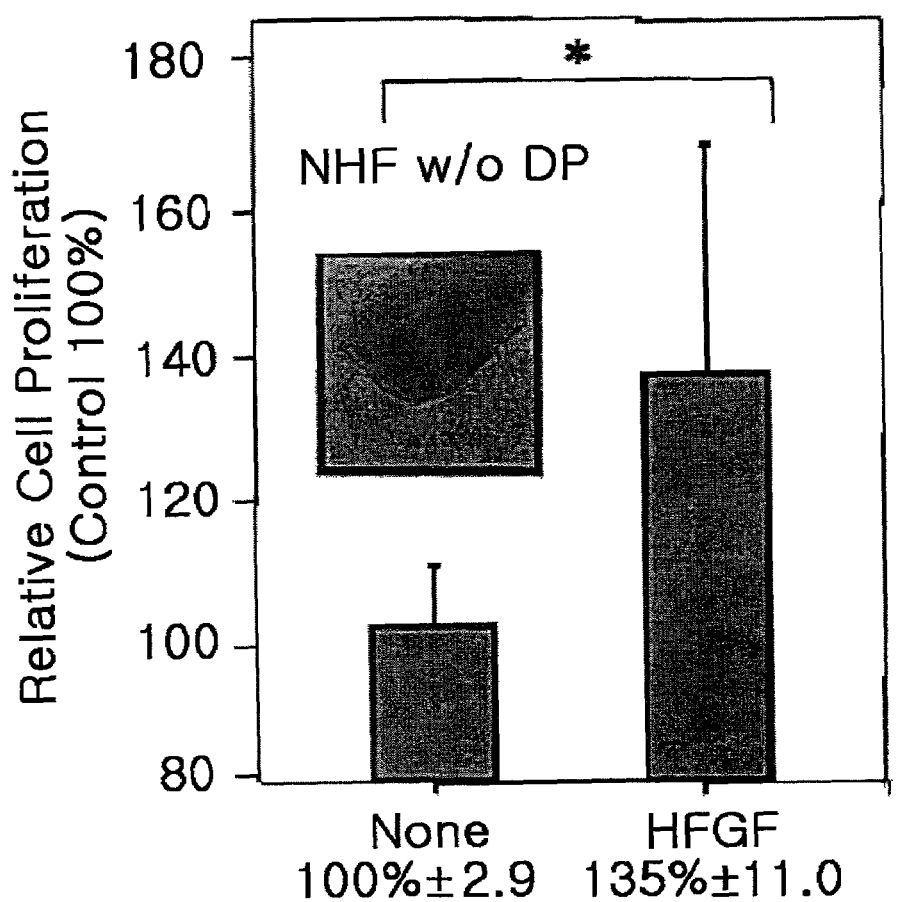
FIG. 6A is a bar graph showing the stimulatory activity of HFGF on proliferation of hair follicles which were derived from a normal person and in which dermal papilla were removed surgically.
Figure 6B:
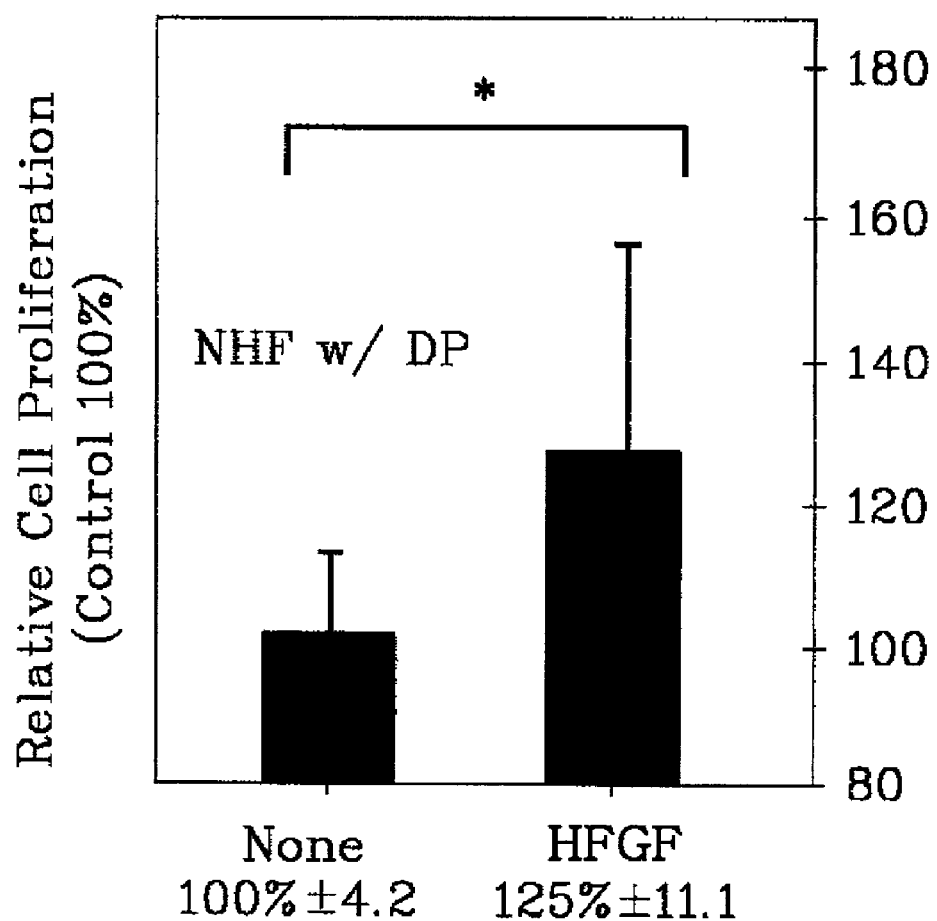
FIG. 6B is a bar graph showing the stimulatory activity of HFGF on proliferation of hair follicle cells with dermal papilla.

Interestingly, HFGF stimulated the proliferation of DP-deleted hair follicle cells with a surprisingly increased level compared to DP-containing hair follicle cells (see FIG. 6A and 6B).

KGF-1 and KGF-2 are closely related proteins in the FGF family. Thus, it is appropriate to compare the stimulatory effect of HFGF to that of KGF-1 and KGF-2.

Accordingly, human hair follicle cells derived from scalp skin were treated with KGF-1, KGF-2 and HFGF, respectively, and, after a lapse of about 48 hours, proliferation rates were measured by colorimetric MTS assay. Further, human hair follicles, in which dermal papilla were removed surgically to exclude any effect by endogenous KGF-2, were treated with KGF-1, KGF-2 and HFGF, respectively.

Figure 7A:
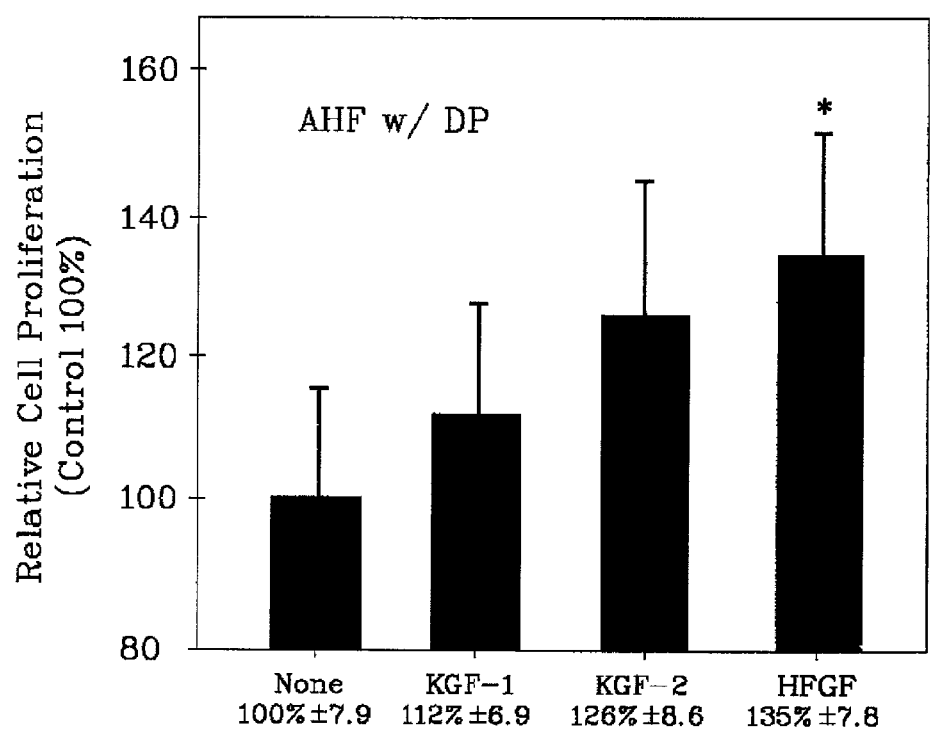
FIG. 7A is a bar graph showing the stimulatory activity of KGF-1, KGF-2 and HFGF, respectively, on proliferation of hair follicles derived from alopecia patients.
Figure 7B:
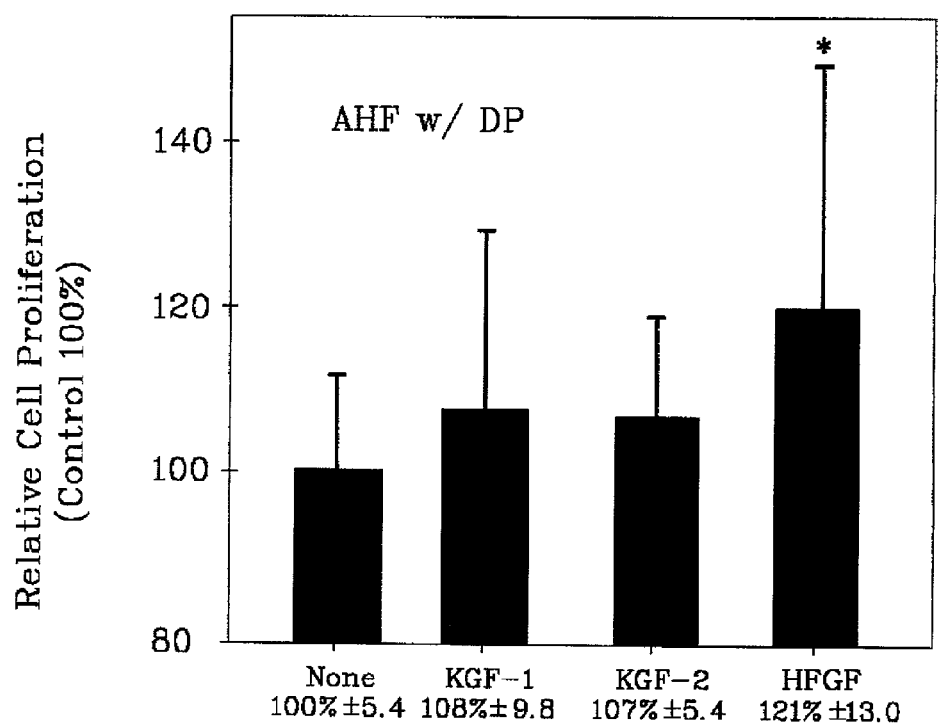
FIG. 7B is a bar graph showing the stimulatory activity of KGF-1, KGF-2 and HFGF, respectively, on the proliferation of hair follicles which were derived from alopecia patients and in which dermal papilla were removed surgically.

The results showed that HFGF significantly stimulated the proliferation of human hair follicle cells compared to KGF-2 and KGF-1, this was independent of removal of dermal papilla (see FIG. 7A and 7B).

The HFGF of the present invention exhibit a stimulatory effect on the proliferation of hair follicle cells. HFGF of the present invention may be used as an effective component of a pharmaceutical composition to prevent or treat alopecia and to promote or accelerate hair growth and hair follicle repair.

In this regard, a HFGF gene encoding HFGF may also be used in a gene therapy regimen to prevent or treat alopecia and for promotion or acceleration of hair growth and hair follicle repair.

Pharmaceutical compositions of the present invention may be prepared by mixing a HFGF protein or a HFGF gene with a pharmaceutically acceptable excipient or adjuvant using traditional formulating methods. Said formulating methods may comprise inserting a HFGF gene into a vector for gene therapy.

In one embodiment, the present invention includes methods for preventing or treating alopecia with a HFGF protein or a gene encoding a HFGF protein. Said methods may comprise administering a pharmaceutical composition containing a HFGF protein or a gene encoding a HFGF protein as an effective component on a patient's scalp skin in a formulation comprising a cream, lotion, gel, ointment, salve, balm, or transdermal patch.

In a further embodiment, a pharmaceutical composition containing a HFGF protein or a gene encoding a HFGF protein may be administered parenterally, i.e. intravenously, subcutaneously, intramuscularly, percutaneously or transdermally, for example, by directly applying to scalp skin.

Definitions

As used herein, the term "allele" refers to any of several alternative forms of a gene.

As used herein, the term "biological activity" particularly refers to a function or set of activities performed by a molecule in a biological context (i.e., in an organism or an in vitro facsimile thereof). Biological activities may include but are not limited to the functions of a HFGF protein or gene encoding a HFGF protein such as a stimulatory effect on hair follicle cell proliferation as well as the promotion or acceleration of hair growth and hair follicle repair. A fusion protein or peptide of the invention is considered to be biologically active if it exhibits one or more biological activities of its native counterpart.

As used herein, the term "gene" refers to any segment of DNA associated with a biological function. Thus, genes include, but are not limited to, coding sequences and/or the regulatory sequences required for their expression. Genes can include nonexpressed DNA segments, such as promoters, enhancers, and/or introns. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, bacterium, fungus, animal or plant.

As used herein, a "heterologous polynucleotide" or a "heterologous nucleic acid" or a "heterologous gene" or an "exogenous DNA segment" refers to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, "heterologous trait" refers to a phenotype imparted to a transformed host cell or transgenic organism by an exogenous DNA segment, heterologous polynucleotide or heterologous nucleic acid.

As used herein, an "isolated" nucleic acid sequence refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

As used herein, two or more DNA coding sequences are said to be "joined" or "fused" when, as a result of in-frame fusions between the DNA coding sequences or as a result of the removal of intervening sequences by normal cellular processing, the DNA coding sequences are translated into a polypeptide fusion.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions in which a codon is altered but still encodes the same amino acid) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605–2608; Cassol et al (1992); Rossolini et al. (1994) Mol. Cell. Probes 8:91–98). The term nucleic acid is used interchangeably with gene, cDNA, and mRNA encoded by a gene.

As used herein, codons are said to be degenerate if they encode the same amino acid.

As used herein, a "mature protein" is a protein that has been post-translationally processed to remove a secretory signal sequence or signal sequence or secretion leader sequence. A mature HFGF protein of the present invention is a protein that is lacking about the first 1, 5, 10, 20, 30, 35, 36, 37, 38, 39, 40, 41, 42, 43, 44 or 45 amino acids of SEQ ID NO: 1. Post-translational processing may occur within a host cell or extracellularly, such as, for example, in an in vitro milieu.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking, in this context, is accomplished by ligation at convenient restriction sites or at adapters or linkers inserted in lieu thereof.

As used herein, the term "phenotype" refers to the observable characteristics of an individual cell, cell culture, bacterium, fungus, animal or plant which results from the interaction between that individual's genetic makeup (i.e., genotype) and the environment.

As used herein, the term "promoter" refers to a region of DNA involved in binding RNA polymerase to initiate transcription.

As used herein, the term "recombinant" refers to a cell, tissue or organism that has undergone transformation with recombinant DNA.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation.

As used herein, the term "transgene" refers to a nucleic acid that is inserted into an organism, host cell or vector in a manner that ensures its function.

As used herein, the term "transgenic" refers to cells, cell cultures, organisms, bacteria, fungi, animals, plants, and progeny of any of the preceding, which have received a foreign or modified gene by one of the various methods of transformation, wherein the foreign or modified gene is from the same or different species than the species of the organism receiving the foreign or modified gene.

As used herein, the term "vector" refers broadly to any plasmid, phagemid or virus encoding an exogenous nucleic acid. The term should also be construed to include non-plasmid, non-phagemid and non-viral compounds which facilitate the transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

As used herein, the term "wild type" refers to a nucleic acid molecule or polynucleotide or polypeptide sequence that is naturally occurring.

Nucleic Acids

Nucleic acid molecules are provided by the present invention. These encode HFGF proteins or fusion proteins comprising HFGF proteins covalently linked or joined to another proteins. Any protein or peptide may be joined to HFGF proteins. The fusion protein may further comprise a linker region, for instance a linker less than about 50, 40, 30, 20, or 10 amino acid residues. The linker can be covalently linked to and between the HFGF protein and the other protein. Host cells and vectors for replicating the nucleic acid molecules and for expressing the encoded proteins are also provided. Any vectors or host cells may be used, whether prokaryotic or eukaryotic. Many vectors and host cells are known in the art for such purposes. It is well within the skill of the art to select an appropriate set for the desired application.

As known in the art "similarity" between two polynucleotides or polypeptides is determined by comparing the nucleotide or amino acid sequence and its conserved nucleotide or amino acid substitutes of one polynucleotide or polypeptide to the sequence of a second polynucleotide or polypeptide. Also known in the art is "identity" which means the degree of sequence relatedness between two polypeptide or two polynucleotide sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

While there exist a number of methods to measure identity and similarity between two polynucleotide or polypeptide sequences, the terms "identity" and "similarity" are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SLAM J. Applied Math., 48: 1073 (1988)). Methods commonly employed to determine identity or similarity between two sequences include, but are not limited to those disclosed in Guide to Huge Computers, Martin J. Bishop, ed., Academic Press, San Diego, 1994, and Carillo, H., and Lipman, D., SIAM J. Applied Math. 48:1073 (1988).

Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, et al., Nucleic Acids Research 12(1):387 (1984)), BLASTP, BLASTN, FASTA (Atschul, et al., J. Molec. Biol. 215:403 (1990)). The degree of similarity or identity referred to above is determined as the degree of identity between the two sequences indicating a derivation of the first sequence from the second. The degree of identity between two nucleic acid sequences may be determined by means of computer programs known in the art such as GAP provided in the GCG program package (Needleman and Wunsch (1970), Journal of Molecular Biology, 48:443–453). For purposes of determining the degree of identity between two nucleic acid sequences for the present invention, GAP is used with the following settings: GAP creation penalty of 5.0 and GAP extension penalty of 0.3.

Vectors

The present invention further provides and utilizes recombinant DNA molecules that contain a coding sequence. As used herein, a recombinant DNA molecule is a DNA molecule that has been subjected to molecular manipulation in situ. Methods for generating recombinant DNA molecules are well known in the art, for example, see Sambrook et al. *Molecular Cloning: A Laboratory Manual*. Cold Spring Harbor, N.Y. Cold Spring Harbor Laboratory Press, 1985. In the preferred recombinant DNA molecules, a coding DNA sequence is operably linked to expression control sequences and/or vector sequences.

The choice of vector and/or expression control sequences to which one of the protein family encoding sequences of the present invention is operably linked depends directly, as well known in the art, on the functional properties desired, e.g., protein expression, and the host cell to be transformed. A vector contemplated by the present invention is at least capable of directing the replication or insertion into the host chromosome, and preferably also expression, of the structural gene included in the recombinant DNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as drug resistance. Typical bacterial drug resistance genes are those that confer resistance to ampicillin, kanamycin or tetracycline, etc.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical vector plasmids are pUC8, pUC9, pBR322 and pBR329 available from BioRad Laboratories, (Richmond, Calif.), pPL and pKK223 available from Pharmacia (Piscataway, N.J.).

Expression vectors compatible with eukaryotic cells, preferably those compatible with vertebrate cells such as kidney cells, can also be used to form recombinant DNA molecules that contain a coding sequence. Eukaryotic cell expression vectors are well known in the art and are available from several commercial sources. Typically, such vectors are provided containing convenient restriction sites for insertion of the desired DNA segment. Typical vectors are pSVL and pKSV-10 (Pharmacia), pBPV-1/pML2d (International Biotechnologies, Inc.), pTDT1 (ATCC, #31255), the vector pCDM8 described herein, and other similar eukaryotic expression vectors.

Eukaryotic cell expression vectors used to construct the recombinant DNA molecules of the present invention may further include a selectable marker that is effective in a eukaryotic cell, preferably a drug resistance selection marker. A preferred drug resistance marker is the gene whose expression results in neomycin resistance, i.e., the neomycin phosphotransferase (neo) gene. (Southern et al. *Journal of Molecular and Applied Genetics*, Vol. 1, no. 4 (1982) pp. 327–341) Alternatively, the selectable marker can be present on a separate plasmid, and the two vectors are introduced by co-transfection of the host cell, and selected by culturing in the appropriate drug for the selectable marker.

Expression units for use in the present invention will generally, though not necessarily, comprise any or all of the following elements, operably linked in a 5' to 3' orientation: a transcriptional promoter, a secretory signal sequence, a DNA sequence encoding a HFGF protein or a HFGF protein joined to a DNA sequence encoding another protein or peptide of interest and a transcriptional terminator. The selection of suitable promoters, signal sequences and terminators will be determined by the selected host cell and will be evident to one skilled in the art and are discussed more specifically below.

Suitable yeast vectors for use in the present invention are described in U.S. Pat. No. 6,291,212, (issued Sep. 18, 2001) and include YRp7 (Struhl et al., Proc. Natl. Acad. Sci. USA 76: 1035–1039, 1978), YEp13 (Broach et al., Gene 8: 121–133, 1979), pJDB249 and pJDB219 (Beggs, Nature 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al. ibid.), URA3 (Botstein et al., Gene 8: 17, 1979), HIS3(Struhl et al., ibid.) or POT1 (Kawasaki and Bell, EP 171,142). Other suitable selectable markers include the CAT gene, which confers chloramphenicol resistance on yeast cells. Preferred promoters for use in yeast include promoters from yeast glycolytic genes (Hitzeman et al., J Biol. Chem. 225: 12073–12080, 1980; Alber and Kawasaki, J. Mol. Appl. Genet. 1: 419–434, 1982; Kawasaki, U.S. Pat. No. 4,599,311) or alcohol dehydrogenase genes (Young et al., in Genetic Engineering of Microorganisms for Chemicals, Hollaender et al., (eds.), p. 355, Plenum, N.Y., 1982; Ammerer, Meth. Enzymol. 101: 192–201, 1983). In this regard, particularly preferred promoters are the TPI1 promoter (Kawasaki, U.S. Pat. No. 4,599,311, 1986) and the ADH2-4$^C$ [see U.S. Pat. No. 6,291,212 promoter (Russell et al., Nature 304: 652–654, 1983). The expression units may also include a transcriptional terminator. A preferred transcriptional terminator is the TPI1 terminator (Alber and Kawasaki, ibid.).

In addition to yeast, proteins of the present invention can be expressed in filamentous fungi, for example, strains of the fungi *Aspergillus*. Examples of useful promoters include those derived from *Aspergillus nidulans* glycolytic genes, such as the ADH3 promoter (McKnight et al., EMBO J. 4: 2093–2099, 1985) and the tpiA promoter. An example of a suitable terminator is the ADH3 terminator (McKnight et al., ibid.). The expression units utilizing such components may be cloned into vectors that are capable of insertion into the chromosomal DNA of *Aspergillus*, for example.

Mammalian expression vectors for use in carrying out the present invention will include a promoter capable of directing the transcription of a cloned gene or cDNA. Preferred promoters include viral promoters and cellular promoters. Preferred viral promoters include the major late promoter from adenovirus 2 (Kaufman and Sharp, Mol. Cell. Biol. 2: 1304–13199, 1982) and the SV40 promoter (Subramani et al., Mol. Cell. Biol. 1: 854–864, 1981). Preferred cellular promoters include the mouse metallothionein 1 promoter (Palmiter et al., Science 222: 809–814, 1983) and a mouse $V_K$ [see U.S. Pat. No. 6,291,212] promoter (Grant et al., Nuc. Acids Res. 15: 5496, 1987). A particularly preferred promoter is a mouse $VH_H$ 8 see U.S. Pat. No. 6,291,212] promoter (Loh et al., ibid.). Such expression vectors may also contain a set of RNA splice sites located downstream from the promoter and upstream from the DNA sequence encoding the HFGF protein. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 E1B region and the human growth hormone gene terminator (DeNoto et al., Nuc. Acids Res. 9: 3719–3730, 1981). A particularly preferred polyadenylation signal is the $V_H$ [see U.S. Pat. No. 6,291,212] gene terminator (Loh et al., ibid.). The expression vectors may include a noncoding viral leader sequence, such as the adenovirus 2 tripartite leader, located between the promoter and the RNA splice sites. Preferred vectors may also include enhancer sequences, such as the SV40 enhancer and the mouse mu. [see U.S. Pat. No. 6,291,212] enhancer (Gillies, Cell 33: 717–728, 1983). Expression vectors may also include sequences encoding the adenovirus VA RNAs.

Transformation

The present invention further provides or utilizes host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH3T3) available from the ATCC as CRL 1658, baby hamster kidney cells (BHK), COS and COS7 cells and like eukaryotic tissue culture cell lines.

Any prokaryotic host can be used to express a recombinant DNA molecule encoding a protein of the invention, particularly peptides and fragments of the full-length receptor protein. The preferred prokaryotic host is *E. coli*.

Transformation of appropriate cell hosts with a recombinant DNA molecule of the present invention is accomplished by well known methods that typically depend on the type of vector used and host system employed. With regard to transformation of prokaryotic host cells, electroporation and salt treatment methods are typically employed, see, for example, Cohen et al., *Proceedings of the National Academy of Science USA*, Vol. 69, no. 8 (1972) pp. 2110–2114; and Maniatis et al., *Molecular Cloning: A Laboratory Mammal.* Cold Spring Harbor, N.Y. Cold Spring Harbor Laboratory Press, 1982). With regard to transformation of vertebrate cells with vectors containing recombinant DNAs, electroporation, cationic lipid or salt treatment methods knew are typically employed, see, for example, Graham et al., *Virology*, Vol. 52, no. 2 (1973) pp. 456–467; and Wigler et al., *Proceedings of the National Academy of Science USA*, Vol. 76 (1979) pp. 1373–1376.

Successfully transformed cells, i.e., cells that contain a recombinant DNA molecule of the present invention, can be identified by well known techniques including the selection for a selectable marker. For example, cells resulting from the introduction of an recombinant DNA of the present invention can be cloned to produce single colonies. Cells from those colonies can be harvested, lysed and their DNA content examined for the presence of the recombinant DNA using a method such as that described by Southern, *Journal of Molecular Biology*, Vol. 98, no. 3 (1975) pp. 503–517; or Berent et al., *Biotechnic and Histochemistry*, Vol. 3 (1985) pp. 208; or the proteins produced from the cell assayed via an immunological method.

Techniques for transforming fungi are well known in the literature, and have been described, for instance, by Beggs (ibid.), Hinnen et al. (Proc. Natl. Acad. Sci. USA 75: 1929–1933, 1978), Yelton et al., (Proc. Natl. Acad. Sci. USA 81: 1740–1747, 1984), and Russell (Nature 301: 167–169, 1983). The genotype of the host cell will generally contain a genetic defect that is complemented by the selectable marker present on the expression vector. Choice of a particular host and selectable marker is well within the level of ordinary skill in the art.

Cloned DNA sequences may be introduced into cultured mammalian cells by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973.) Other techniques for introducing cloned DNA sequences into mammalian cells, such as electroporation (Neumann et al., EMBO J. 1: 841–845, 1982), or lipofection may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. A particularly preferred amplifiable marker is the DHFR$^r$ [see U.S. Pat. No. 6,291,212] cDNA (Simonsen and Levinson, Proc. Natl. Adac. Sci. USA 80: 2495–2499, 1983). Selectable markers are reviewed by Thilly (Mammalian Cell Technology, Butterworth Publishers, Stoneham, Mass.) and the choice of selectable markers is well within the level of ordinary skill in the art.

Host Cells

Host cells for use in practicing the present invention include prokaryotic and eukaryotic cells capable of being transformed or transfected with exogenous DNA and grown in culture, such as cultured mammalian, insect, fungal, plant, bacterial, viral and baculoviral cells. Fungal cells, including species of yeast (e.g., *Saccharomyces* spp., *Schizosaccharomyces* spp.) may be used as host cells within the present invention. Examples of other fungal cells are cells of filamentous fungi, e.g. *Aspergillus* spp., *Neurospora* spp., *Fusarium* spp. or *Trichoderma* spp., in particular strains of *A. oryzae*, *A. nidulans* or *A. niger*. The use of *Aspergillus* spp. for the expression of proteins have been described in e.g., EP 272,277 and EP 230,023. The transformation of *F. oxysporum* may, for instance, be carried out as described by Malardier et al. (1989) Gene 78:147–156.

Strains of the yeast *Saccharomyces cerevisiae* are particularly preferred. In a preferred embodiment, a yeast cell, or more specifically, a *Saccharomyces cerevisiae* host cell that contains a genetic deficiency in a gene required for asparagine-linked glycosylation of glycoproteins is used. *S. cerevisiae* host cells having such defects may be prepared using standard techniques of mutation and selection. Ballou et al. (J. Biol. Chem. 255: 5986–5991, 1980) have described the isolation of mannoprotein biosynthesis mutants that are defective in genes which affect asparagine-linked glycosylation. Briefly, mutagenized *S. cerevisiae* cells were screened using fluoresceinated antibodies directed against the outer mannose chains present on wild-type yeast. Mutant cells that did not bind antibody were farther characterized and were found to be defective in the addition of asparagine-linked oligosaccharide moieties. To optimize production of the heterologous proteins, it is preferred that the host strain carries a mutation, such as the *S. cerevisiae* pep4 mutation (Jones, Genetics 85: 23–33, 1977), which results in reduced proteolytic activity. Host strains containing mutations in other protease encoding regions are also contemplated.

Host cells containing DNA constructs of the present invention are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. The growth medium will be generally selected for cells containing the DNA construct by, for example, drug selection or deficiency in an essential nutrient which are complemented by the selectable marker on the DNA construct or co-transfected with the DNA construct. Yeast cells, for example, are preferably grown in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1 M and 1.5 M., preferably at 0.5 M or 1.0 M.

Cultured mammalian cells are generally grown in commercially available serum-containing or serum-free media. Selection of a medium appropriate for the particular cell line used is within the level of ordinary skill in the art. Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Secretory Signal Sequences

The terms secretory signal sequences or signal sequences or secretion leader sequences are used interchangeably and are described, for example in U.S. Pat. No. 6,291,212 and U.S. Pat. No. 5,547,871, both of which are herein incorporated by reference in their entirety. Secretory signal sequences or signal sequences or secretion leader sequences encode secretory peptides. A secretory peptide is an amino acid sequence that acts to direct the secretion of a mature polypeptide or protein from a cell. Secretory peptides are generally characterized by a core of hydrophobic amino acids and are typically (but not exclusively) found at the amino termini of newly synthesized proteins. Very often the secretory peptide is cleaved from the mature protein during secretion. Secretory peptides may contain processing sites that allow cleavage of the signal peptide from the mature protein as it passes through the secretory pathway. Processing sites may be encoded within the signal peptide or may be added to the signal peptide by, for example, in vitro mutagenesis. A mature HFGF protein of the present invention is a protein that is lacking about the first 1, 5, 10, 20, 30, 35, 36, 37, 38, 39, 40, 41, 42, 43, 44 or 45 amino acids of SEQ ID NO:1. Certain secretory peptides may be used in concert to direct the secretion of polypeptides and proteins. One such secretary peptide that may be used in combination with other secretory peptides is the third domain of the yeast Barrier protein. Secretory signal sequences or signal sequences or secretion leader sequences are required for a complex series of post-translational processing steps which result in secretion of a protein. If an intact signal sequence is present, the protein being expressed enters the lumen of the rough endoplasmic reticulum and is then transported through the Golgi apparatus to secretory vesicles and is finally transported out of the cell. Generally, the signal sequence immediately follows the initiation codon and encodes a signal peptide at the amino-terminal end of the protein to be secreted. In most cases, the signal sequence is cleaved off by a specific protease, called a signal peptidase. Preferred signal sequences improve the processing and export efficiency of recombinant protein expression using viral, mammalian or yeast expression vectors.

Detection of Secreted Proteins

Assays for detection of secreted, biologically active HFGF protein or HFGF fusion proteins may include Western transfer, protein blot or colony filter. A Western transfer filter may be prepared using the method described by Towbin et al. (Proc. Natl. Acad. Sci. USA 76: 4350–4354, 1979). Briefly, samples are electrophoresed in a sodium dodecyl-sulfate polyacrylamide gel. The proteins in the gel are electrophoretically transferred to nitrocellulose paper. Protein blot filters may be prepared by filtering supernatant samples or concentrates through nitrocellulose filters using, for example, a Minifold (Schleicher & Schuell, Keene, N.H.). Colony filters may be prepared by growing colonies on a nitrocellulose filter that has been laid across an appropriate growth medium. In this method, a solid medium is preferred. The cells are allowed to grow on the filters for at least 12 hours. The cells are removed from the filters by washing with an appropriate buffer that does not remove the proteins bound to the filters. A preferred buffer comprises 25 mM Tris-base, 19 mM glycine, pH 8.3, 20% methanol.

Isolation of HFGF Proteins and Fusion Proteins

Biologically active HFGF proteins or fusion proteins may be isolated from the medium of host cells grown under conditions that allow the secretion of the biologically active proteins or they may be isolated by cell lysis followed by purification of the resultant cell lysate. Where HFGF protein of the invention is secreted, the cell material is removed from the culture medium, and the biologically active HFGF protein or HFGF fusion protein is isolated using isolation techniques known in the art. Suitable isolation techniques include precipitation and fractionation by a variety of chromatographic methods, including gel filtration, ion exchange chromatography and affinity chromatography. A particularly preferred purification method is affinity chromatography on an iron binding or metal chelating column or an immunoaffinity chromatography using an antibody directed against the HFGF protein or HFGF fusion protein. The antibody is preferably immobilized or attached to a solid support or substrate. A particularly preferred substrate is CNBr-activated Sepharose (Pharmacia LKB Technologies, Inc., Piscataway, N.J.). By this method, the medium is combined with the antibody/substrate under conditions that will allow binding to occur. The complex may be washed to remove unbound material, and the HFGF protein or HFGF fusion protein is released or eluted through the use of conditions unfavorable to complex formation. Particularly useful methods of elution include changes in pH, wherein the immobilized antibody has a high affinity for the ligand at a first pH and a reduced affinity at a second (higher or lower) pH; changes in concentration of certain chaotropic agents or salts, such as NaCl, for example; or through the use of detergents.

HFGF Mutants

Within the scope of the present invention are HFGF proteins or HFGF fusion proteins wherein one or more amino acid substitutions, insertions or deletions occur in coding region of Met 1 to Arg 68 of HFGF or N- or C-termini of HFGF. When carrying out nucleotide substitutions using techniques for accomplishing site-specific mutagenesis that are well known in the art, the encoded amino acid changes are preferably of a minor nature, that is, conservative amino acid substitutions, although other, non-conservative, substitutions are contemplated as well. Specifically contemplated are small deletions or insertions, typically of one to about 30 amino acids; small amino- or carboxyl-terminal extensions, such as an amino-terminal methionine residue, or small linker peptides of less than 50, 40, 30, 20 or 10 residues linking a HFGF protein and another protein or peptide; or a small extension that facilitates purification, such as a poly-histidine tract, an antigenic epitope or a binding domain, such as a GST fusion.

Examples of conservative amino acid substitutions are substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

Non-conservative substitutions encompass substitutions of amino acids belonging to one group by amino acids belonging to another group. For example, a non-conservative substitution would include the substitution of a polar amino acid by a hydrophobic amino acid. For a general description of nucleotide substitution, see e.g. Ford et al. (1991) Protein Expression and Purification 2:95–107. Non-conservative substitutions, deletions and insertions are particularly useful to produce mutant HFGF proteins with altered biological properties.

For the polypeptides and proteins of the invention, the following system is followed for designating amino acids in accordance with the following conventional list:

TABLE 1

AMINO ACIDS AND SYMBOLS

| AMINO ACID | ONE-LETTER SYMBOL | THREE-LETTER SYMBOL |
|---|---|---|
| Alanine | A | Ala |
| Arginine | R | Arg |
| Asparagine | N | Asn |
| Aspartic Acid | D | Asp |
| Cysteine | C | Cys |
| Glutamine | Q | Gln |
| Glutamic Acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Production of Fusion Proteins

The present invention further provides methods for producing a fusion protein of the invention using nucleic acid molecules described herein. In general terms, the production of a recombinant form of a protein typically involves the following steps.

A nucleic acid molecule is first obtained that encodes HFGF protein fusion protein of the invention. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally, the recombinant protein is isolated from the medium or from the cells; recovery and purification of the protein may not be necessary in some instances where some impurities may be tolerated.

Each of the foregoing steps can be accomplished in a variety of ways. For example, the construction of expression vectors that are operable in a variety of hosts is accomplished using appropriate replicons and control sequences, as set forth above. The control sequences, expression vectors, and transformation methods depend on the type of host cell used to express the gene as discussed in detail earlier, and are otherwise known to persons skilled in the art. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce a desired recombinant protein.

Any expression system may be used, including yeast, bacterial, animal, plant, eukaryotic and prokaryotic systems. In some embodiments, yeast, mammalian cell culture and transgenic animal or plant production systems are preferred. In other embodiments, yeast systems that have been modified to reduce native yeast glycosylation, hyper-glycosylation or proteolytic activity may be used. In still further embodiments, bacterial expression systems may be used.

Pharmaceutical Formulations

The HFGF proteins and HFGF fusion proteins of the invention may be administered to a patient in need thereof using standard administration protocols. For instance, the agents of the present invention can be provided alone, or in combination, or in sequential combination with other agents that modulate a particular pathological process. As used herein, two agents are said to be administered in combination when the two agents are administered simultaneously or are administered independently in a way such that the agents will act at the same or almost the same time.

The agents of the present invention can be administered via, topical, parenteral, subcutaneous, intravenous, intramuscular, intraperitoneal, transdermal, or buccal routes. For example, an agent may be administered locally to a site via microinfusion or by topical application in a cream, gel, lotion, ointment, salve, balm, aqueous solution or patch. Alternatively, or concurrently, administration may be by the oral route. The dosage administered will be dependent upon the age, health, and weight of the recipient, kind of concurrent treatment, if any, frequency of treatment, and the nature of the desired effect.

The present invention further provides compositions containing one or more proteins of the invention. While individual needs vary, determination of optimal ranges of effective amounts of each protein is within the skill of the art. Typical dosages of protein for topical formulations comprise from about 0.1 ng to about 100 ng per ml of the formulation, preferably from about 10 ng to about 50 ng, most preferably about 30 ng.

In addition to the pharmacologically active protein, the compositions of the present invention may contain suitable pharmaceutically acceptable carriers comprising excipients and auxiliaries that facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol and dextran. Optionally, the suspension may also contain stabilizers. Liposomes can also be used to encapsulate the agent for delivery into the cell.

The pharmaceutical formulation for systematic administration according to the invention may be formulated for enteral, parenteral or topical administration. Indeed, all three types of formulations may be used simultaneously to achieve systematic administration of the active ingredient. Suitable formulations for oral administration include hard or soft gelatin capsules, pills, tablets, including coated tablets, elixirs, suspensions, syrups or inhalations and controlled release forms thereof.

In practicing the methods of this invention, the agents of this invention may be used alone or in combination, or in combination with other therapeutic or diagnostic agents. In certain preferred embodiments, the proteins of this invention may be co-administered along with other compounds typically prescribed for these conditions according to generally accepted medical practice. The proteins of this invention can be utilized in vivo for mammals, such as humans, sheep, horses, cattle, pigs, dogs, cats, rats and mice, or in vitro.

Transgenic Animals

The production of transgenic non-human animals that contain HFGF protein encoding construct of the instant invention is contemplated in one embodiment of the present invention.

The successful production of transgenic, non-human animals has been described in a number of patents and publications, such as, for example U.S. Pat. No. 6,291,740 (issued Sep. 18, 2001); U.S. Pat. No. 6,281,408 (issued Aug. 28, 2001); and U.S. Pat. No. 6,271,436 (issued Aug. 7, 2001) the contents of which are hereby incorporated by reference in their entireties.

The ability to alter the genetic make-up of animals, such as domesticated mammals including cows, pigs, goats, horses, cattle, and sheep, allows a number of commercial applications. These applications include the production of animals which express large quantities of exogenous proteins in an easily harvested form (e.g., expression into the milk or blood), the production of animals with increased weight gain, feed efficiency, carcass composition, milk production or content, disease resistance and resistance to infection by specific microorganisms and the production of animals having enhanced growth rates or reproductive performance. Animals which contain exogenous DNA sequences in their genome are referred to as transgenic animals.

The most widely used method for the production of transgenic animals is the microinjection of DNA into the pronuclei of fertilized embryos (Wall et al., J. Cell. Biochem. 49:113 [1992]). Other methods for the production of transgenic animals include the infection of embryos with retroviruses or with retroviral vectors. Infection of both pre- and post-implantation mouse embryos with either wild-type or recombinant retroviruses has been reported (Janenich, Proc. Natl. Acad. Sci. USA 73:1260 [1976]; Janenich et al., Cell 24:519 [1981]; Stuhlmann et al., Proc. Natl. Acad. Sci. USA 81:7151 [1984]; Jahner et al., Proc. Natl. Acad Sci. USA 82:6927 [1985]; Van der Putten et al., Proc. Natl. Acad Sci. USA 82:6148–6152 [1985]; Stewart et al., EMBO J. 6:383–388 [1987]).

An alternative means for infecting embryos with retroviruses is the injection of virus or virus-producing cells into the blastocoele of mouse embryos (Jahner, D. et al., Nature 298:623 [1982]). The introduction of transgenes into the germline of mice has been reported using intrauterine retroviral infection of the midgestation mouse embryo (Jahner et al., supra [1982]). Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832 [1990]; and Haskell and Bowen, Mol. Reprod. Dev., 40:386 [1995]. PCT International Application WO 90/08832 describes the injection of wild-type feline leukemia virus B into the perivitelline space of sheep embryos at the 2 to 8 cell stage. Fetuses derived from injected embryos were shown to contain multiple sites of integration.

U.S. Pat. No. 6,291,740 (issued Sep. 18, 2001) describes the production of transgenic animals by the introduction of exogenous DNA into pre-maturation oocytes and mature, unfertilized oocytes (i.e., pre-fertilization oocytes) using retroviral vectors which transduce dividing cells (e.g., vectors derived from murine leukemia virus [MLV]). This patent also describes methods and compositions for cytomegalovirus promoter-driven, as well as mouse mammary tumor LTR expression of various recombinant proteins.

U.S. Pat. No. 6,281,408 (issued Aug. 28, 2001) describes methods for producing transgenic animals using embryonic stem cells. Briefly, the embryonic stem cells are used in a mixed cell co-culture with a morula to generate transgenic animals. Foreign genetic material is introduced into the embryonic stem cells prior to co-culturing by, for example, electroporation, microinjection or retroviral delivery. ES cells transfected in this manner are selected for integration of the gene via a selection marker such as neomycin.

U.S. Pat. No. 6,271,436 (issued Aug. 7, 2001) describes the production of transgenic animals using methods including isolation of primordial germ cells, culturing these cells to produce primordial germ cell-derived cell lines, transforming both the primordial germ cells and the cultured cell lines, and using these transformed cells and cell lines to generate transgenic animals. The efficiency at which transgenic animals are generated is greatly increased, thereby allowing the use of homologous recombination in producing transgenic non-rodent animal species.

Gene Therapy

The use of HFGF protein constructs for gene therapy is contemplated in one embodiment of this invention. The HFGF protein constructs of the present invention are ideally suited to gene therapy treatments.

The polynucleotide of the invention can be applied to the scalp through delivery of nucleic acid molecules. The delivery of nucleic acid molecules can be accomplished by many means known in the art. Gene delivery vehicles (GDVs) are available for delivery of polynucleotides to cells or tissue for expression. For example, a nucleic acid sequence of the invention can be administered either locally or systematically in a GDV. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle is preferably a viral vector and, more preferably, a retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector. See generally, Jolly, Cancer Gene Therapy 1:51–64 (1994); Kimura, Human Gene Therapy 5:845–852 (1994), Connelly, Human Gene Therapy 6:185–193 (1995), and Kaplitt, Nature Genetics 6:148–153 (1994).

Delivery of the gene therapy constructs of this invention into cells is not limited to the above-mentioned viral vectors. Other delivery methods and media may be employed such as nucleic acid expression vectors, polycationic condensed DNA linked or unlinked to killed adenovirus alone (Curiel, Hum Gene Ther 3:147–154 (1992), ligand linked DNA (Wu, J. Biol. Chem. 264:16985–16987 (1989), eucaryotic cell delivery vehicles cells (U.S. Pat. No. 6,015,686), deposition of photopolymerized hydrogel materials, hand-held gene transfer particle gun (U.S. Pat. No. 5,149,655), ionizing radiation (U.S. Pat. No. 5,206,152 and PCT Patent Publication No. WO 92/11033), nucleic charge neutralization or fusion with cell membranes. Additional approaches are described in Philip, Mol. Cell. Biol. 14:2411–2418 (1994) and in Woffendin, Proc. Natl. Acad. Sci. 91:1581–585 (1994). Particle mediated gene transfer may be employed, for example see U.S. provisional application No. 60/023, 867. Briefly, the nucleotide sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes, that can act as gene delivery vehicles are described in U.S. Pat. No. 5,422,120, PCT Patent Publication Nos. WO 95/13796, WO 94/23697, and WO 91/144445, and EP No. 524,968.

The nucleic acid molecule may be introduced into the scalp using the injectable carrier alone; liposomal preparations are preferred for methods in which in vitro transfections of cells obtained from the scalp are carried out. The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide. Alternatively, an even more prolonged effect can be achieved by introducing the DNA sequence into the cell by means of a vector plasmid having the DNA sequence inserted therein. Preferably, the plasmid further comprises a replicator. Such plasmids are well known to those skilled in the art, for example, plasmid pBR322, with replicator pMB1, or plasmid pMK16, with replicator ColE1 (Ausubel, Current Protocols in Molecular Biology, John Wiley and Sons, New York (1988) .sctn.II:1.5.2.

It is possible to obtain long term administration of a polypeptide to the scalp by introducing a naked DNA sequence operatively coding for the polypeptide interstitially into the scalp, whereby cells of the tissue produce the polypeptide for at least one month or at least 3 months, more preferably at least 6 months. In addition, a method for obtaining transitory expression of a polypeptide in the scalp can be achieved by introducing a naked mRNA sequence operatively coding for the polypeptide interstitially into the scalp, whereby cells of the tissue produce the polypeptide for less than about 20 days, usually less than about 10 days, and often less than 3 or 5 days.

One important aspect of the invention is a method for treatment of alopecia, comprising the steps of introducing a therapeutic amount of a composition comprising a nucleic acid molecule operatively coding for the polypeptide of the invention in a pharmaceutically acceptable injectable carrier in vivo into the scalp of patients suffering from alopecia, whereby the nucleic acid molecule is taken up into the cells and the polypeptide is produced in vivo. Preferably, the nucleic acid molecule is a naked nucleic acid molecule and the composition is introduced interstitially into the scalp.

The nucleic acid may be either a DNA or RNA sequence. When the nucleic acid is DNA, it can also be a DNA sequence which is itself non-replicating, but is inserted into a plasmid, and the plasmid further comprises a replicator. The DNA may be a sequence engineered so as not to integrate into the host cell genome. The nucleic acid sequences may code for a polypeptide which is either contained within the cells or secreted therefrom, or may comprise a sequence which directs the secretion of the peptide. The DNA sequence may also include a promoter sequence. In one preferred embodiment, the DNA sequence includes a cell-specific promoter that permits substantial transcription of the DNA only in predetermined scalp. The DNA may also code for a polymerase for transcribing the DNA, and may comprise recognition sites for the polymerase and the injectable preparation may include an initial quantity of the polymerase. In one preferred embodiment, the nucleic acid is DNA coding for both a polypeptide and a polymerase for transcribing the DNA, and the DNA includes recognition sites for the polymerase and the injectable preparation further includes a means for providing an initial quantity of the polymerase in the cell. The initial quantity of polymerase may be physically present together with the DNA. Alternatively, it may be provided by including mRNA coding therefor, which mRNA is translated by the cell. In this embodiment of the invention, the DNA is preferably a plasmid. Preferably, the polymerase is phage T7 polymerase and the recognition site is a T7 origin of replication sequence.

The pharmaceutical compositions containing the nucleic acid molecule according to the invention can be formulated for the purposes of topical, cutaneous, parenteral, subcutaneous, and transdermal administrations and the like. The pharmaceutical compositions of the invention preferably contain a pharmaceutical vehicle which is acceptable for an injectable formulation, especially for direct injection on the scalp. They can in particular be isotonic, sterile solutions or dry compositions, especially lyophilized, which, by addition, depending on the situation, of sterilized water or of physiological serum, make it possible to prepare injectable solutions. The doses of nucleic acid used for injection, as well as the number of administrations, can be varied according to various parameters, and especially as a function of the method of administration used, severity of the alopecia, age of patients, or alternatively of the desired duration of treatment. Containers used in the present invention will usually have at least 1, preferably at least 5 or 10, and more preferably at least 50 or 100 micrograms of polynucleotide, to provide one or more unit dosages. For many applications, the container will have at least 500 micrograms or 1 milligram, and often will contain at least 50 or 100 milligrams of polynucleotide.

In addition, gene therapy is described in a number of U.S. patents including U.S. Pat. No. 6,225,290 (issued May 1, 2001); U.S. Pat. No. 6,187,305 (issued Feb. 13, 2001); and U.S. Pat. No. 6,140,111 (issued Oct. 31, 2000). U.S. Pat. No. 6,225,290 provides methods and constructs whereby intestinal epithelial cells of a mammalian subject are genetically altered to operatively incorporate a gene which expresses a protein which has a desired therapeutic effect. Intestinal cell transformation is accomplished by administration of a formulation composed primarily of naked DNA, and the DNA may be administered orally. Oral or other intragastrointestinal routes of administration provide a simple method of administration, while the use of naked nucleic acid avoids the complications associated with use of viral vectors to accomplish gene therapy. The expressed protein is secreted directly into the gastrointestinal tract and/or blood stream to obtain therapeutic blood levels of the protein thereby treating the patient in need of the protein. The transformed intestinal epithelial cells provide short or long term therapeutic cures for diseases associated with a deficiency in a particular protein or which are amenable to treatment by overexpression of a protein. U.S. Pat. No. 6,187,305 provides methods of gene or DNA targeting in cells of vertebrate, particularly mammalian, origin. Briefly, DNA is introduced into primary or secondary cells of vertebrate origin through homologous recombination or targeting of the DNA, which is introduced into genomic DNA of the primary or secondary cells at a preselected site.

U.S. Pat. No. 6,140,111 (issued Oct. 31, 2000) describes retroviral gene therapy vectors. The disclosed retroviral vectors include an insertion site for genes of interest and are capable of expressing high levels of the protein derived from the genes of interest in a wide variety of transfected cell types. Also disclosed are retroviral vectors lacking a selectable marker, thus rendering them suitable for human gene therapy in the treatment of a variety of disease states without the co-expression of a marker product, such as an antibiotic. These retroviral vectors are especially suited for use in certain packaging cell lines. The ability of retroviral vectors to insert into the genome of mammalian cells have made them particularly promising candidates for use in the genetic therapy of genetic diseases in humans and animals. Genetic therapy typically involves (1) adding new genetic material to patient cells in vivo, or (2) removing patient cells from the body, adding new genetic material to the cells and reintroducing them into the body, i.e., in vitro gene therapy. Discussions of how to perform gene therapy in a variety of cells using retroviral vectors can be found, for example, in U.S. Pat. Nos. 4,868,116, issued Sep. 19, 1989, and 4,980,286, issued Dec. 25, 1990 (epithelial cells), WO89/07136 published Aug. 10, 1989 (hepatocyte cells), EP 378,576 published Jul. 25, 1990 (fibroblast cells), and WO89/05345 published Jun. 15, 1989 and WO/90/06997, published Jun. 28, 1990 (endothelial cells), the disclosures of which are incorporated herein by reference in their entireties.

The successful use of gene therapy to express protein has also been described in non-patent literature. In one case, gene therapy via injection of an adenovirus vector containing a gene encoding a soluble fusion protein consisting of cytotoxic lymphocyte antigen 4 (CTLA4) and the Fc portion of human immunoglubulin G1 was recently shown in Ijima et al. (Jun. 10, 2001) Human Gene Therapy (United States) 12/9:1063–77. In this application of gene therapy, a murine model of type II collagen-induced arthritis was successfully treated via intraarticular injection of the vector.

Hair Transplantation

In a typical hair transplantation procedure, grafts of skin containing hair are removed from the back or sides of the scalp (donor area) of the individual and are transplanted to other areas, that is, the bald or thinning area (recipient area). To place the grafts onto these areas, a number of incisions are made in the scalp. The incisions are then cleaned and a graft is inserted into each incision. Hair transplantation includes a minigraft for placing only a small number of hairs into the incisions, a micrograft for placing a single hair in the incisions (also, referred to as one-haired minigraft), and a follicular unit hair transplantation.

The minigraft utilizes 2 to 6 hairs per graft. It provides good hair density to the transplanted area. It is ideally suited for the top portion of the head where the appearance of hair density is desirable. A variety of techniques have been employed to transplant minigrafts. In one attempt, the use of a dilator has been proposed. According to this method, an 18 or 20 gauge hypodermic needle is employed to form an incision. A dilator is then placed in the incision to dilate the incision. After removal of the dilator, the minigraft is inserted. Over time, the incision shrinks so that the skin will support the graft. Alternatively, with the quick "Slit Technique", the surgeon makes multiple slits on the bald scalp with a knife blade. This can be accomplished in a very short period of time. Following making of the quick skin slits, the hair grafts are planted into these bald skin slits, without removing (decreasing) the amount of balded scalp. The original bald scalp remains discernible as bald gaps between the slits of hair grafts. The transplanted hair grafts may also be compressed by the tight bald scalp tissue on both sides of the skin slits when the hair grafts and hair follicles are inserted. In other proposed methods, punches have been employed to punch a small diameter hole in the scalp. The graft is then placed in the cylindrical opening left by the punch. In yet another proposed method, a #11 blade (a Lancet blade) has been employed to form an incision for receiving a minigraft. Since the Lancet blade is angled, this method includes the additional step of translating the blade downward at an angle of 45 degree after the initial insertion so that the bottom of the incision has a constant depth. Having a constant depth is desirable so that the hair follicles in the graft will all be transplanted at the same depth. In a similar procedure, the use of a No-Kor vented needle (Becton Dickinson and Co, Rutherford, N.J.) has been proposed for creating incisions for receiving 1 to 3 haired minigrafts. Such a method is described in, Dominic A. Brandy and Michael Meshkin, Utilization of No-Kor Needles For Slit-micrografting, J Dermatol Surg Oncol, 20:336–339 (1994).

The micrograft was developed in the 1990s to transplant 1 to 2 hairs per graft. It is ideally used for the front area of the scalp, at the upper part of the forehead, so as to create a soft, natural frontal hairline. The use of the micrografis is a major improvement over the old hair plugs used in the 1980s, which resulted in the "corn-row" hairline with the "Barbie doll" appearance.

Follicular unit hair transplantation is a completely different process. Scalp hair follicles actually grow in small groupings or units of 1, 2, 3 or occasionally 4 hair follicles per unit. This naturally occurring grouping of follicles is called a "follicular unit". A thin linear segment of hair-bearing skin is first harvested from areas where there is a surplus of follicles that are genetically superior. The thin linear opening in the skin is then carefully and meticulously closed with sutures. The remaining pencil line incision is typically easily hidden by the hair. Using magnification, "follicular unit" grafts are then fashioned from the tiny naturally occurring groupings of hair follicles. These grass seed size "follicle grafts" (not "hairy skin grafts"), each containing a single "follicular unit", can then be transplanted into closely spaced needle size openings within the areas of hair loss.

HFGF proteins of the present invention have a pharmacological effect on hair follicle cell proliferation. It is therefore understood that the pretreatment of scalp hair follicles or grafts with the HFGF proteins of the present invention will promote or accelerate hair implantation. Accordingly, the present invention provides a method for transplanting hair in a subject which comprises supplementing scalp hair follicles or grafts with the polypeptide comprising an amino acid sequence of Ser 69 to Ser 208 of SEQ ID NO: 1 and transplanting the supplemented hair grafts or follicles with the polypeptide to the bald or thinning area of said subject.

Diagnosis of Alopecia

The present invention also relates to the use of HFGF proteins or nucleic acid molecule encoding said proteins in diagnosis of alopecia. Detection of HFGF proteins or nucleic acid molecules encoding said proteins of the present invention will provide a diagnostic tool that can add or define a diagnosis of alopecia or susceptibility to a disease which results from under-expression or altered expression of HFGF. Individuals carrying point mutation in the human KGF-2 gene in which a codon for Lys 87 is replaced with either codon for Glu or codon for Asp may be detected at the DNA level by a variety of techniques. Proteins or nucleic acids for diagnosis may be obtained from a patient's cells, such as from blood, urine, saliva, scalp tissue biopsy and autopsy material. The genomic DNA may be used directly for detection or may be amplified enzymatically by using PCR prior to analysis (Saiki et al., Nature 324:163–166 (1986)). RNA or cDNA may also be used in the same ways. As an example, PCR primers complementary to the nucleic acid encoding HFGF can be used to identify and analyze HFGF proteins expression and/or point mutation in KGF-2. For example, deletions and insertions can be detected by a change in size of the amplified product in comparison to the normal genotype. Point mutations can be identified by hybridizing amplified DNA to radiolabeled HFGF RNA or alternatively, radiolabeled HFGF antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing fortnamide gradient gels in which the mobilities of different DNA fragments are retarded in the gel at different positions according to their specific melting or partial melting temperatures (see, e.g., Myers et al., Science 230:1242 (1985)).

Sequence changes at specific locations also may be revealed by nuclease protection assays, such as RNase and Si protection or the chemical cleavage method (e.g., Cotton et al., Proc. Natl. Acad. Sci. (USA) 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP")) and Southern blotting of genomic DNA. In addition to more conventional gel-electrophoresis and DNA sequencing, mutations also can be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a HFGF gene. This can be accomplished using a variety of well known techniques and libraries, which generally are available commercially. The genomic DNA is used for in situ chromosome mapping using well known techniques for this purpose. Typically, in accordance with routine procedures for chromosome mapping, some trial and error may be necessary to identify a genomic probe that gives a good in situ hybridization signal.

The present invention also relates to diagnostic assays such as quantitative and diagnostic assays for detecting levels of HFGF protein in cells and tissues, including determination of normal and abnormal levels. Thus, for instance, a diagnostic assay in accordance with the invention for detecting under-expression of HFGF proteins compared to normal control tissue samples may be used to detect the prognosis of alopecia. Assay techniques that can be used to determine levels of HFGF proteins of the present invention, in a sample derived from a host, for example blood or scalp tissue are well-known to those of skill in the art. Such assay methods include radioimmunoassays, competitive-binding assays, Western Blot analysis and ELISA assays. Among these, ELISAs are frequently preferred. An ELISA assay initially comprises preparing an antibody specific to HFGF, preferably a monoclonal antibody. In addition, a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HFGF proteins attached to the polystyrene dish. Unbound monoclonal antibodies are washed out with buffer. The reporter antibody linked to horseradish peroxidase is placed in the dish resulting in binding of the reporter antibody to any monoclonal antibody bound to HFGF protein. Unattached reporter antibodies are then washed out. Reagents for peroxidase activity, including a colorimetric substrate are then added to the dish. Immobilized peroxidase, linked to HFGF protein through the primary and secondary antibodies, produces a colored reaction product. The amount of color developed in a given time period indicates the amount of HFGF protein present in the sample. Quantitative results typically are obtained by reference to a standard curve.

A competition assay may be employed wherein antibodies specific to HFGF protein attached to a solid support and labeled HFGF protein and a sample derived from the host are passed over the solid support and the amount of label detected attached to the solid support can be correlated to a quantity of HFGF protein in the sample.

Accordingly, the present invention provides a method for diagnosing alopecia in a subject comprising collecting a blood or tissue sample from said subject and detecting HFGF proteins in said sample.

Unless otherwise defined, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

Without further description, it is believed that a person of ordinary skill in the art can, using the preceding description and the following illustrative examples, make and utilize the present invention and practice the disclosed methods. The following working examples therefore, specifically point out the preferred embodiments of the present invention, and are not to be construed as limiting in any way the remainder of the disclosure.

EXAMPLES

Example 1

Isolation of Hair Follicles

Hair follicles with a morphological structure characteristic of anagen were obtained from human scalp skin both of normal persons (persons without alopecia) and alopecia patients.

Example 2

Isolation of the Human HFGF cDNA

Reverse transcription was performed using total RNA extracted by Trizol (Gibco BRL) from hair follicles obtained in Example 1. More specifically, total RNA (50–1000 nanograms) isolated from human hair follicles was incubated for 60 min at 37° C. in a reaction mixture of about 200 microliters containing 300 units of Moloney murine leukemia virus reverse transcriptase, 15 units of human placenta RNase inhibitor and 0.5 micrograms of a random hexa-deoxynucleotide primer, which resulted in the production of a cDNA solution. To specifically amplify human HFGF cDNA from said cDNA solution, PCR was performed using a GeneAmp PCR System 9600 (Perkin-Elmer) for 30 cycles in a reaction mixture containing an aliquot of the above cDNA solution, 0.05 units/microliter Taq DNA polymerase, and 4 pmol/microliter of each of the sense primer, atgtggaaatggatactgac, (SEQ ID NO:3) and the antisense primer, ctatgagtgtaccaccattgg, (SEQ ID NO:4) to amplify a sequence corresponding to the sequence of the $1^{st}$ to $208^{th}$ amino acids of human KGF-2.

Five clones were randomly selected, and their nucleotide sequences were determined. Specifically, the amplified cDNA of 627 base-pairs as shown in FIG. 9 (SEQ ID NO:2) was cloned into the vector pGEM-T (Promega Biotech) and the nucleotide sequence of the cloned cDNA was determined with an Applied Biosystems model 377 DNA sequencer (Perkin-Elmer) using dideoxy terminator cycle sequencing (Applied Biosystems).

As a result, one of the five clones was identified with a sequence that encodes for a polypeptide having an amino acid sequence wherein the lysine residue at position 87 of the human KGF-2 protein is replaced by glutamic acid. The isolated cDNA was analogous to that of human KGF-2 cDNA, suggesting that it was a human HFGF protein (HFGF) cDNA clone. The nucleotide sequence of the coding region of the human HFGF cDNA (627 nucleotides) (SEQ ID NO:2) is shown in FIG. 9, which is highly homologous (99.5%) to that of human KGF-2.

The above human HFGF cDNA was inserted into the pGEM-T vector to construct pGEM-T-KGF-2A which express HFGF protein of the present invention. The pGEM-T vector contains a T7 Sp6 RNA polymerase dual promotor (−17 to +3) and lac operator (200 to 216).

The nucleotide sequence of SEQ ID NO:2 allowed the elucidation of the complete amino acid sequence (208 amino acids) of human HFGF, wherein the $4^{th}$ to the $117^{th}$ nucleotides encode a putative signal sequence of HFGF. The amino acid sequence of HFGF (SEQ ID NO:1) is shown in FIG. 8.

Example 3

Analysis of Expression of HFGF and its Receptor FGFR2IIIb mRNA by RT-PCR

The mRNA level of HFGF from human hair follicles was analyzed to investigate the expression level of HFGF. The mRNA of HFGF was specifically converted to cDNA by RT-PCR using oligonucleotide primers, ttggtcaggacatggtg (SEQ ID NO:5) and ctatgagtgtaccaccattgg (SEQ ID NO:6) which flank a 427-base pair coding sequence (nucleotides 119 to 627) of human HFGF.

Specifically, total RNA (100 micrograms) extracted from hair follicles was converted to cDNA by PCR performed for 40 cycles at 94° C. for 1 min, 55° C. for 1 min, and 72° C. for 2 min in a reaction mixture containing 15 units of Moloney murine leukemia virus reverse transcriptase and the oligonucleotide primers shown as SEQ ID NO:5 and SEQ ID NO:6.

To investigate the expression level of HFGF receptor, i.e. FGFR2 IIIb, RT-PCR was performed using the oligonucleotide primers, ggagaatgaatacgggtcc (SEQ ID NO:7) and ggttggcctgccctatatata (SEQ ID NO:8) which flank a 350-base pair coding sequence (nucleotides 699 to 1049) of human FGFR2IIIb.

The mRNA of FGFR2IIIb was specifically converted to cDNA by RT-PCR having a reaction profile consisting of one cycle at 94° C. for 1 min, followed by 35 cycles at 94° C. for 1 min, 58° C. for 30 sec, and 72° C. for 1 min with a final extension of 5 min at 72° C.

The RT-PCR products were analyzed in a 1.5% agarose gel and the mRNA level of β-actin was also analyzed as an internal control.

Figure 3:
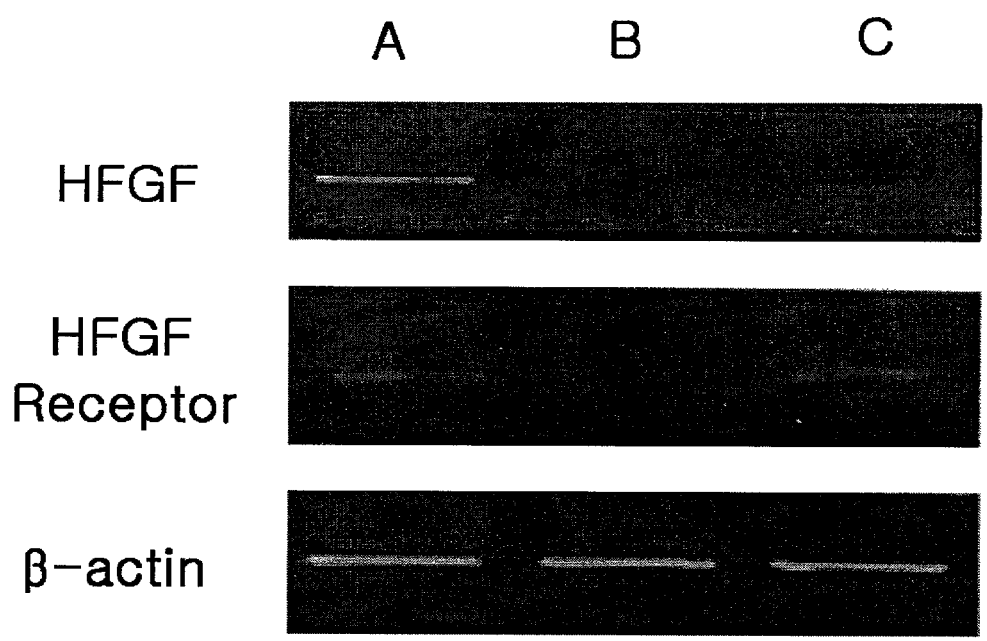
FIG. 3 shows the expression levels of HFGF and HFGF receptor, respectively, in hair follicles which were derived from human scalp skin of normal persons or alopecia patients.
Figure 4:
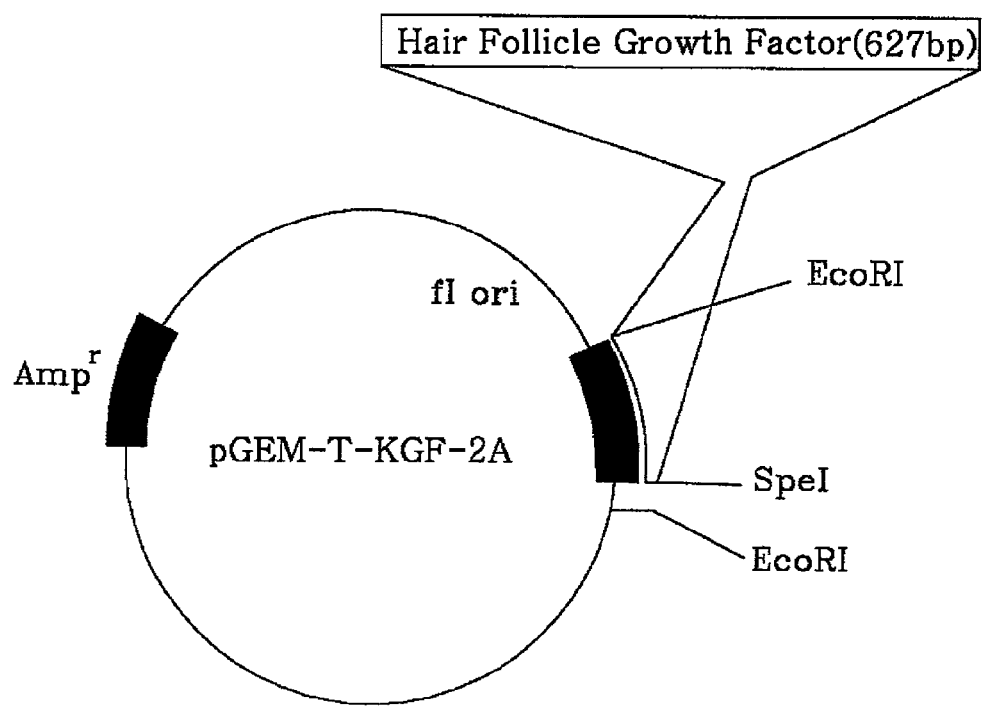
FIG. 4 shows a restriction map of the pGEM-T-KGF-2A constructed by inserting HFGF DNA having the nucleotide sequence of SEQ ID NO:2 into the pGEM-T vector.

As shown in FIG. 3, the results of agarose gel analysis demonstrate that cDNA encoding HFGF from normal persons (persons without alopecia) was detected while no cDNA encoding HFGF from alopecia patients was detected. This is in contrast to studies involving the detection of HFGF receptor cDNA in which HFGF receptor cDNA was detected in persons with and without alopecia.

Additionally, as shown in Table 2, HFGF cDNA is absent in seven of seven human hair follicles from alopecia patients while that of normal hair follicles shows HFGF expression in four of seven with a statistically significant difference ($P<0.05$).

TABLE 2

HFGF expression in human hair follicles

| Hair follicles | Expressed | Absent |
|---|---|---|
| Normal | 4/7 (57%) | 3/7 (43%) |
| Alopecia | 0/7 (0%) | 7/7 (100%) |

The foregoing results suggest that silent carriers who are normal in appearance have a reduced expression level of HFGF in their hair follicles, probably due to an inherited trait. These persons are very likely to develop alopecia.

Example 4

Preparation of Recombinant HFGF

The cDNA encoding the $40^{th}$ to the $208^{th}$ amino acids of human HFGF (hHFGF) of SEQ ID NO:1 was amplified using human HFGF cDNA (described in Example 2) as a template by PCR for 25 cycles using Taq DNA polymerase and the following primers, ggatccttggtcaggacatggtg (SEQ ID NO:9) and gaattcctatgagtgtaccaccattgg (SEQ ID NO:10). The amplified region corresponded to that encoding the putative mature growth factor following secretion and cleavage of the signal sequence.

The PCR product was subcloned into the pET9c plasmid (Novagen) and *E. coli* BL21(DE3) was transformed with the pET9c-BFGF.

The transformant produced by the above process was cultured for 48 hours and lysed. The cell lysate was then applied to a heparin-Sepharose column.

Analysis of successive fractions of increasing NaCl concentration eluted from the heparin-Sepharose column determined that the majority of hHFGF eluted with the 1.0 M NaCl fraction, as determined by silver staining of proteins separated by SDS-PAGE, although some protein also eluted in the 0.8 and 1.2 M NaCl fractions.

The apparent molecular mass of the polypeptide was approximately 20 kDa, consistent with the predicted molecular weight. Amino acid analysis of a sample of protein eluted at 1.0 M NaCl confirmed that the preparation consisted of substantially pure HFGF, whose amino terminus was in agreement with that predicted from the sequence.

Example 5

Preparation of Recombinant HFGF using GST-fusion System

The cDNA of hHFGF amplified according to Example 4 was digested with restriction enzymes EcoRI and BamHI and ligated in the EcoRI/BamHI site of the pGEX-2T expression vector. The resultant construct, pGEX-2T-KGF2A recombinant vector was transfected into *E. coli* BL21 (DE3) by heat shock for 30 min at 42° C. The transformant produced by the above process was cultured for 48 hours and lysed.

The cell lysate was applied directly to a glutathione column (Pharmacia Biotech) pre-equilibrated with 50 mM Tris-HCl (pH 8.0). The thrombin-treated column was left over-night (14–16 hours) for cleavage at room temperature before elution (Sigma). Proteins bound to glutathione beads were eluted with glutathione in 50 mM Tris-HCl (pH 8.0). The fraction containing recombinant HFGF was subsequently applied to a Heparin column (Pharmacia Biotech). Recombinant HFGF was eluted with a linear gradient of 0–2.0 M NaCl in 50 mM Tris-HCl (pH 8.0). The recombinant HFGF fraction was dialyzed overnight against phosphate-buffered saline and subsequently applied to PyroSep-C (Tanabe Pharmaceuticals, Japan) for removal of endotoxin.

The apparent molecular mass of HFGF identified by running it on agarose gel was approximately 20 kDa and that of GST-HFGF was 45 kDa, consistent with the predicted molecular weight (see FIG. 2).

Example 6

Determination of Mitogenic Activity of Recombinant HFGF

Isolated human hair follicles are maintained in individual wells of 24-well multiwell plates containing 1 ml of KBM media (Clonetics) supplemented with 100 U/ml penicillin, 10 ng/ml hydrocortisone, 75 µg/ml bovine pituitary extract in an atmosphere of 5% $CO_2$/95% air.

The cell growth of hair follicles was measured by colorimetric MTS assays. Specifically, isolated human hair follicles were treated with HFGF at different concentrations from 10, 30 and 100 ng/ml for forty-eight hours before measuring by MTS assay. In these studies, HFGF produced as in Example 4 was utilized.

Single hair follicle was then plated in a 96-well microtiter per well, and proliferation was measured 4 h later using a colorimetric MTS assay according to the manufacturer's suggestions (Promega). In each experiment, observations (n=8 hair follicles per group) were performed and the values are reported as mean ±standard error (S.E.). In the proliferation assay, the negative control was evaluated using untreated hair follicle cells.

As seen in FIG. 5, the addition of HFGF resulted in dose-dependent of stimulation of human hair follicle cells with a maximum stimulatory effect observed at a concentration of 30 ng/ml HFGF.

Example 7

Determination of Molecular Mechanism of HFGF Activity

Like tooth or feather-bud development, hair follicle morphogenesis is governed by epithelial-mesenchymal interactions, between hair placode keratinocytes and fibroblasts of underlying mesenchymal condensations.

Accordingly, the molecular mechanism of HFGF activity may be suggested by assessing the effects of administration of HFGF on hair follicle cell proliferation in organ culture.

Further, since KGF-2 exists in human hair follicles from normal persons (persons without alopecia), it is intended to exclude any effects caused by an endogenous KGF-2 from dermal papilla. That is, HFGF was used to treat culture media containing human hair follicles from a normal person in which dermal papilla (DP) were removed surgically.

Interestingly, as shown in FIG. 6A and 6B, HFGF stimulate DP-deleted hair follicle cells with the increased percentage of 135%±11.1 (P<0.05) cell proliferation compared to DP-containing hair follicle cells (125%±11.0).

Example 8

Comparison of Stimulatory Activities Between KGF-1, KGF-2 and HFGF

Human hair follicle cells derived from scalp skin were treated with KGF-1, KGF-2 and HFGF respectively and after a lapse of about 48 hours their proliferation rates were measured by colorimetric MTS assay. Further, human hair follicles, in which dermal papilla were removed surgically to exclude any effect caused by endogenous KGF-2, were treated with KGF-1, KGF-2 and HFGF, respectively.

As a result, HFGF stimulated significantly human hair follicle cells derived from alopecia patient's scalp by 135%±7.8 compared to 126%±8.6 for KGF-2 and 112%±6.9 for KGF-1 as shown in FIG. 7A. The significant stimulatory effect of HFGF was also shown in human DP-deleted hair follicle cells from an alopecia patient's scalp as 121%±13.0 (FIG. 7B). As noted in the foregoing summary, detailed description and examples, the HFGF of the present invention is a new form of KGF-2, wherein HFGF comprises an amino acid sequence with a glutamic acid residue at position 87 and can be isolated from hair follicles of human scalp skin. The HFGF of the present invention has a characteristic reduced expression in hair follicles derived from alopecia patients and has a stimulatory effect on hair follicle cell proliferation. Therefore, HFGF can be used to prevent or treat alopecia and to promote or accelerate hair growth and hair follicle repair.

Formulation Example 1: Ointment

An ointment base was prepared using the following ingredients and composition (w/w):

| Ingredient | Composition |
| --- | --- |
| White petrolatum | 25% |
| Stearyl alcohol | 25% |
| Propylene glycol | 12% |
| Sodium lauryl sulfate | 1% |
| Methylparaben | 0.025% |
| Propylparaben | 0.015% |
| Purified water, q.s. ad | 100% |

The stearyl alcohol and white petrolatum were melted in a steam bath and warmed to about 75° C. The water was heated to 75° C. and the sodium sulfate, propylene glycol, methylparaben, and propylparaben were added to the water. The aqueous phase was added and stirred until congealed to form an ointment base.

100 ml of an ointment base obtained above was mixed with 0.003 g of isolated HFGF polypeptide to afford an ointment, which is to be applied topically to males with alopecia.

Formulation Example 2: Cream

A cream base was prepared using the following ingredients and composition (w/w):

| Phase | Ingredient | |
| --- | --- | --- |
| Oleagenous | Stearyl alcohol | 15% |
| | Beeswax | 8% |
| | Sorbitan monooleate | 1.25% |
| Aqueous | Sorbitol solution (70% USP) | 7.5% |
| | Polysorbate 80 | 3.75% |
| | Methylparaben | 0.025% |
| | Propylparaben | 0.015% |
| | Purified water, q.s. ad | 100% |

The oil phase and water phase were heated to 70° C. The oil phase was added slowly to the aqueous phase with stirring to form a crude emulsion. The resulting emulsion was cooled to about 55° C. and homogenized. The cooling was continued with agitation until it congealed.

100 ml of a cream base obtained above was mixed with 0.003 ng of isolated HFGF polypeptide to afford an ointment, which is to be applied topically to males with alopecia.

Formulation Example 3: Gel

A gel base was prepared using the following ingredients and composition (w/w):

| Ingredient | Composition |
| --- | --- |
| Methocel 90 H.C. 4000 | 0.8% |
| Carbopol 934 | 0.24% |
| Propylene glycol | 16.7% |
| Methylparaben | 0.015% |
| Sodium hydroxide, q.s. ad | pH 7 |
| Purified water, q.s. ad | 100% |

The Methocel was dispersed in 40 ml of hot (85° C.) water. The resulting dispersion was chilled overnight in a refrigerator to effect solution. The Carbopol 934 was dispersed in 20 ml of water. The pH of the dispersion was adjusted to 7.0 by adding sufficient 1% sodium hydroxide solution (about 12 ml was required per 100 ml) and the volume was brought to 40 ml with purified water. The methylparaben was dissolved in the propylene glycol. The Methodcel, Carbopol 934 and propylene glycol fractions obtained above were mixed carefully to avoid the incorporation of air.

100 ml of a cream base obtained above was mixed with 0.003 ng of isolated HFGF polypeptide to afford an ointment, which is to be applied topically to males with alopecia.

Formulation Example 4: Paste

A paste base was prepared using the following ingredients and composition (w/w):

| Ingredient | Composition |
| --- | --- |
| Zinc oxide | 25% |
| Starch | 25% |
| Calamine | 5% |
| White petrolatum, q.s. ad | 100% |

The calamine was titrated with the zinc oxide and starch. The resulting mixture was incorporated uniformly in the petrolatum by levigation in a glass slab with a spatula to afford a paste base.

100 ml of a paste base obtained above was mixed with 0.003 ng of isolated HFGF polypeptide to afford an ointment, which is to be applied topically to males with alopecia.

All references, patents and patent applications cited herein are hereby incorporated by reference in their entireties. It must be noted that as used in this specification and the appended claims, the singular forms "a", "an" and "the" include plural referents unless the context clearly dictates otherwise. Thus, for example, reference to "a method of producing a HFGF protein recombinantly" includes one or more methods or steps of the type described herein.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

What is claimed is:

1. An isolated polypeptide having the amino acid sequence of SEQ ID NO: 1.

2. The isolated polypeptide of claim 1 wherein Glu 87 is replaced by Asp 87.

3. An isolated polypeptide having the amino acid sequence of amino acids 40 to 208 of SEQ ID NO: 1.

4. The isolated polypeptide of claim 3 wherein Glu 87 is replaced by Asp 87.

5. An isolated polypeptide having the amino acid sequence of amino acids 69 to 208 of SEQ ID NO: 1.

6. The isolated polypeptide of claim 5 wherein Glu 87 is replaced by Asp 87.

7. A composition comprising the polypeptide of any one of claims 1, 3, 5, 2, 4, or 6 and a carrier.

8. A method for stimulating hair follicle growth comprising administering the composition of claim 7 to hair follicles.

9. The method of claim 8 wherein said composition contains the polypeptide in an amount of about 0.1 to about 100 ng/ml of the composition.

10. The method of claim 9 wherein said composition contains the polypeptide in an amount of 30 ng/ml of the composition.

11. The method of claim 8 wherein said composition is administered topically to hair follicles of a scalp.

12. The method of claim 11 wherein said composition is a topical formulation selected from the group consisting of solution, cream, ointmnent, gel, and lotion.

13. The method of claim 11 wherein said composition is applied through the use of a transdermal patch.

14. An isolated nucleic acid molecule that encodes a polypeptide having the amino acid sequence of SEQ ID NO:1.

15. The isolated nucleic acid molecule of claim 14 wherein the codon encoding glutamic acid at position 87 of SEQ ID NO:1 is replaced by with a codon encoding aspartic acid.

16. An isolated nucleic acid molecule that encodes a polypeptide having the amino acid sequence of amino acids 40 to 208 of SEQ ID NO: 1.

17. The isolated nucleic acid molecule of claim 16 wherein the codon encoding glutamic acid at position 87 of SEQ ID NO:1 is replaced by with a codon encoding aspartic acid.

18. An isolated nucleic acid molecule that encodes a polypeptide having the amino acid sequence of amino acids 69 to 208 of SEQ ID NO: 1.

19. The isolated nucleic acid molecule of claim 18 wherein the codon encoding glutamic acid at position 87 of SEQ ID NO:1 is replaced by with a codon encoding aspartic acid.

20. The isolated nucleic acid molecule of any one of claims 14, 16, 18, 15, 17 or 19 wherein said molecule is DNA or RNA.

21. A composition comprising the nucleic acid molecule of any one of claims 14, 16, 18, 15, 17, or 19 and a carrier.

22. A vector comprising a nucleic acid molecule encoding a polypeptide having the amino acid sequence of SEQ ID NO:1.

23. The vector of claim 22 wherein the nucleic acid molecule is DNA.

24. The vector of claim 23 wherein the vector further comprises a promoter and a transcription terminator, said promoter being operably linked to the DNA encoding the polypeptide having the amino acid sequence of SEQ ID NO:1, and said DNA being operably linked to the transcription terminator.

25. The vector of claim 22 wherein said vector is pGEM-T-KGF-2A.

26. A vector comprising a nucleic acid molecule encoding a polypeptide having the amino acid sequence of amino acids 40 to 208 of SEQ ED NO:1.

27. The vector of claim 26 wherein the nucleic acid molecule is DNA.

28. The vector of claim 27 wherein the vector further comprises a promoter and a transcription terminator, said promoter being operably linked to the DNA encoding the polypeptide having the amino acid sequence of amino acids 40 to 208 of SEQ ID NO: 1, and said DNA being operably linked to the transcription terminator.

29. A vector comprising a nucleic acid molecule encoding a polypeptide having the amino acid sequence of amino acids 69 to 208 of SEQ ID NO:1.

30. The vector of claim 29 wherein the nucleic acid molecule is DNA.

31. The vector of claim 30 wherein the vector further comprises a promoter and a transcription terminator, said promoter being operably linked to the DNA encoding the polypeptide having the amino acid sequence of amino acids 69 to 208 of SEQ ID NO: 1, and said DNA being operably linked to the transcription terminator.

32. The vector of any of claims 24, 28 or 31 wherein the DNA encodes a polypeptide wherein Glu 87 is replaced by Asp 87.

33. A host cell transfected by a vector comprising:
a transcription promoter,
a DNA encoding a polypeptide having the amino acid sequence of amino acids 69 to 208 of SEQ ID NO: 1, and
a transcription terminator,
wherein the promoter is operably linked to the DNA and the DNA is operably linked to the transcription terminator.

34. The host cell of claim 33 wherein the DNA encodes a polypeptide wherein Glu 87 is replaced by Asp 87.

35. The host cell of any of claims 33, or 34 wherein the cell is *E. coli*.

36. A method of producing a polypeptide having the amino acid sequence of amino acids 69 to 208 of SEQ ID NO: 1 comprising:
culturing a host cell transfected by a vector comprising a transcription promoter, a DNA encoding the polypeptide having the amino acid sequence of amino acids 69 to 208 of SEQ ID NO: 1, and a transcription terminator, wherein the promoter is operably linked to the DNA and the DNA is operably linked to the transcription terminator, under conditions such that the polypeptide is expressed; and
isolating said polypeptide from the culture.

37. A method of producing a polypeptide having the amino acid sequence of SEQ ID NO:1 comprising:
culturing a host cell transfected by a vector comprising a transcription promoter, a DNA encoding a polypeptide having the amino acid sequence of SEQ ID NO: 1, and a transcription terminator, wherein the promoter is operably linked to the DNA and the DNA is operably linked to the transcription terminator, under conditions such that the polypeptide is expressed; and
isolating said polypeptide from the culture.

38. A method of producing a polypeptide having the amino acid sequence of amino acids 40 to 208 of SEQ ID NO: 1 comprising:
culturing a host cell transfected by a vector comprising a transcription promoter, a DNA encoding the polypeptide having the amino acid sequence of amino acids 40 to 208 of SEQ ID NO: 1, and a transcription terminator, wherein the promoter is operably linked to the DNA and the DNA is operably linked to the transcription terminator, under conditions such that the polypeptide is expressed; and
isolating said polypeptide from the culture.

39. The method of claims 36, 37 or 38 wherein the DNA encodes a polypeptide wherein Glu 87 is replaced by Asp 87.

40. A method for transplanting hair in a subject comprising
supplementing scalp hair follicles or grafts with a polypeptide having the amino acid sequence of amino acids 69 to 208 of SEQ ID NO: 1; and
transplanting the supplemented hair grafts or follicles with the polypeptide to the bald or thinning area of said subject.

* * * * *

SEQUENCE LISTING

<160> NUMBER OF SEQ ID NOS: 10

<210> SEQ ID NO 1
<211> LENGTH: 208
<212> TYPE: PRT
<213> ORGANISM: Homo sapiens

<400> SEQUENCE: 1

```
Met Trp Lys Trp Ile Leu Thr His Cys Ala Ser Ala Phe Pro His Leu
1               5                   10                  15

Pro Gly Cys Cys Cys Cys Phe Leu Leu Phe Leu Val Ser Ser
            20                  25                  30

Val Pro Val Thr Cys Gln Ala Leu Gly Gln Asp Met Val Ser Pro Glu
            35                  40                  45

Ala Thr Asn Ser Ser Ser Ser Phe Ser Ser Pro Ser Ser Ala Gly
        50                  55                  60

Arg His Val Arg Ser Tyr Asn His Leu Gln Gly Asp Val Arg Trp Arg
65                  70                  75                  80

Lys Leu Phe Ser Phe Thr Glu Tyr Phe Leu Lys Ile Glu Lys Asn Gly
                85                  90                  95

Lys Val Ser Gly Thr Lys Lys Glu Asn Cys Pro Tyr Ser Ile Leu Glu
                100                 105                 110

Ile Thr Ser Val Glu Ile Gly Val Val Ala Val Lys Ala Ile Asn Ser
                115                 120                 125

Asn Tyr Tyr Leu Ala Met Asn Lys Lys Gly Lys Leu Tyr Gly Ser Lys
        130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
                180                 185                 190

Arg Arg Lys Asn Thr Ser Ala His Phe Leu Pro Met Val Val His Ser
        195                 200                 205
```

<210> SEQ ID NO 2
<211> LENGTH: 627
<212> TYPE: DNA
<213> ORGANISM: Homo sapiens

<400> SEQUENCE: 2

```
atgtggaaat ggatactgac acattgtgcc tcagcctttc cccacctgcc cggctgctgc      60
tgctgctgct ttttgttgct gttcttggtg tcttccgtcc ctgtcacctg ccaagccctt     120
ggtcaggaca tggtgtcacc agaggccacc aactcttctt cctcctcctt ctcctctcct     180
tccagcgcgg gaaggcatgt gcggagctac aatcaccttc aaggagatgt ccgctggaga     240
aagctattct ctttcaccga gtactttctc aagattgaga gaacgggaa ggtcagcggg      300
```

```
accaagaagg agaactgccc gtacagcatc ctggagataa catcagtaga aatcggagtt      360
gttgccgtca aagccattaa cagcaactat tacttagcca tgaacaagaa ggggaaactc      420
tatggctcaa aagaatttaa caatgactgt aagctgaagg agaggataga ggaaaatgga      480
tacaatacct atgcatcatt taactggcag cataatggga ggcaaatgta tgtggcattg      540
aatgaaaaag gagctccaag gagaggacag aaaacacgaa ggaaaaacac ctctgctcac      600
tttcttccaa tggtggtaca ctcatag                                         627
```

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3

```
atgtggaaat ggatactgac a                                                21
```

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4

```
ctatgagtgt accaccattg g                                                21
```

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5

```
ttggtcagga catggtg                                                     17
```

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6

```
ctatgagtgt accaccattg g                                                21
```

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7

```
ggagaatgaa tacgggtcc                                                   19
```

<210> SEQ ID NO 8
<211> LENGTH: 21
<212> TYPE: DNA
<213> ORGANISM: Artificial Sequence
<220> FEATURE:

-continued

```
<223> OTHER INFORMATION: Primer

<400> SEQUENCE: 8
ggttggcctg ccctatatat a                                              21

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ggatccttgg tcaggacatg gtg                                            23

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gaattcctat gagtgtacca ccattgg                                        27
```